US009994839B2

(12) United States Patent
Lo et al.

(10) Patent No.: US 9,994,839 B2
(45) Date of Patent: Jun. 12, 2018

(54) MICROFLUIDIC DEVICES TO EXTRACT, CONCENTRATE AND ISOLATE MOLECULES

(71) Applicant: The Regents of the University of California, Oakland, CA (US)

(72) Inventors: Yu-Hwa Lo, San Diego, CA (US); Wen Qiao, La Jolla, CA (US); Junlan Song, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 267 days.

(21) Appl. No.: 14/761,606

(22) PCT Filed: Jan. 16, 2014

(86) PCT No.: PCT/US2014/011909
§ 371 (c)(1),
(2) Date: Jul. 16, 2015

(87) PCT Pub. No.: WO2014/113598
PCT Pub. Date: Jul. 24, 2014

(65) Prior Publication Data
US 2015/0368635 A1 Dec. 24, 2015

Related U.S. Application Data

(60) Provisional application No. 61/753,402, filed on Jan. 16, 2013.

(51) Int. Cl.
*G01N 27/453* (2006.01)
*C12N 15/10* (2006.01)
(Continued)

(52) U.S. Cl.
CPC .... *C12N 15/1003* (2013.01); *B01L 3/502715* (2013.01); *B01L 3/502753* (2013.01);
(Continued)

(58) Field of Classification Search
CPC ........ G01N 27/44791; C12Q 2565/125; C12N 15/01; C12N 15/003; C12N 15/1013;
(Continued)

(56) References Cited

U.S. PATENT DOCUMENTS 6,007,690 A   12/1999  Nelson et al.
8,425,749 B1* 4/2013  Ravula .................... B03C 5/026
                                                      181/141
(Continued)

FOREIGN PATENT DOCUMENTS

EP         2390350      11/2011
WO       1991006679     5/1991
(Continued)

OTHER PUBLICATIONS

Asbury et al., "Trapping of DNA by dielectrophoresis," Electrophoresis 2002, 23, 2658-2666.*
(Continued)

*Primary Examiner* — Alexander S Noguerola
(74) *Attorney, Agent, or Firm* — Perkins Coie LLP

(57) ABSTRACT

Methods, systems, and devices are disclosed for capturing, concentrating, and isolating molecules in a fluid. In one aspect, a device includes a substrate formed of a material that is electrically insulating, a microfluidic channel made of an electrically insulating material formed on the substrate to carry a biofluid containing molecules including nucleic acids, an array of electrodes formed on the surface along a parallel direction of the microfluidic channel constituting a capture region, in which the array of electrodes are operable to produce an electric field across the microfluidic channel that creates an electrostatic attractive force on the nucleic acids to immobilize them in the capture region, and a chamber formed on the substrate of the electrically insulating material and connected to the microfluidic channel, the
(Continued)

chamber configured to have a volume less than that of the microfluidic channel, in which, when the nucleic acids are released from immobilization in the capture region, the released nucleic acids are collected in the chamber.

40 Claims, 10 Drawing Sheets

(51) Int. Cl.
   B01L 3/00       (2006.01)
   G01N 27/447     (2006.01)
(52) U.S. Cl.
   CPC .... *B01L 3/502761* (2013.01); *C12N 15/1013* (2013.01); *C12N 15/1017* (2013.01); *G01N 27/44791* (2013.01); *B01L 2200/0647* (2013.01); *B01L 2200/0668* (2013.01); *B01L 2300/06* (2013.01); *B01L 2300/0636* (2013.01); *B01L 2300/0645* (2013.01); *B01L 2300/0681* (2013.01); *B01L 2300/0816* (2013.01); *B01L 2300/0877* (2013.01); *B01L 2400/0415* (2013.01); *C12Q 2565/125* (2013.01)
(58) Field of Classification Search
   CPC ............ C12N 15/1017; C12N 15/1003; B03C 5/005–5/028
   See application file for complete search history.

(56) References Cited

U.S. PATENT DOCUMENTS

| | | | |
|---|---|---|---|
| 2004/0241699 | A1 | 12/2004 | Zocchi et al. |
| 2008/0202933 | A1 | 8/2008 | Hu |
| 2008/0227185 | A1* | 9/2008 | Schonfeld ........ G01N 27/44782 435/287.2 |
| 2008/0234144 | A1* | 9/2008 | Ho ...................... C12Q 1/6813 506/39 |
| 2009/0071830 | A1 | 3/2009 | Vann et al. |
| 2009/0152215 | A1 | 6/2009 | Ahn et al. |
| 2009/0269767 | A1 | 10/2009 | Soderlund et al. |
| 2010/0173310 | A1 | 7/2010 | Bousse et al. |
| 2010/0181195 | A1 | 7/2010 | Garcia Tello |
| 2011/0039717 | A1 | 2/2011 | Kwong et al. |
| 2012/0208189 | A1 | 8/2012 | Xu et al. |
| 2012/0258459 | A1 | 10/2012 | Huang |
| 2015/0361483 | A1 | 12/2015 | Lo et al. |

FOREIGN PATENT DOCUMENTS

| | | |
|---|---|---|
| WO | 2005098029 | 10/2005 |
| WO | 2006032044 | 3/2006 |
| WO | 2011147931 | 12/2011 |
| WO | 2012151289 A2 | 11/2012 |

OTHER PUBLICATIONS

Chao et al., "Review: Microfluidic single-cell analysis of intracellular compounds," J. R. Soc. Interface (2008) 5, S139-S150.*
Ramadan et al., "Simultaneous cell lysis and bead trapping in a continuous flow microfluidic device," Sensors and Actuators B, 113 (2006) 944-955.*
Geng et al., "Modulating DNA adsorption on silica beads using an electrical switch," Chem. Commun., 2009, 800-802.*
Chhina et al., "Microfluidc system to detect DNA amplicons using agglutination technique," J. Micromech. Microeng. 22 (2012) 115038 (8 pages).*
MicroRNAs in Blood May be Biomarkers of Pancreatic Cancer. NIH, News. Sep. 1, 2009, http://www.nih.gov/news/health/sep2009/nci-01.htm.
Cantin et al., "Discrimination between exosomes and HIV-1: Purification of both vesicles from cell-free supernatants." Journal of Immunological Methods, vols. 1-2, 2008, pp. 21-30.
Chen et al. 10, "Microfiuidic isolation and transcriptome analysis of serum microvesicles." s.l. : The Royal Society of Chemistry, 2010, Lab on a Chip, pp. 505-511.
Cho et al., "Human Mammalian Cell Sorting using Microfabricated Fluorescence Activated Cell Sorter." 2010, Lab on a Chip, vol. DOI:10, p. 1039:C000136H.
Ding et al., "Single-molecule mechanical identification and sequencing," Nature Methods, vol. 9, No. 4, 367-374, Apr. 2012.
Geekiyanage et al., "Blood serum miRNA non-invasive biomarkers for Alzheimer's disease.", Experimental Neurology, 235(2), Jun. 2012, pp. 491-496.
Godin et al., "Microfluidics and photonics for Bio-System-on-a-chip: A review of advancements in technology towards a microfluidics flow cytometry chip." Journal of Biophotonics, 2008, pp. 355-376.
Heinze et al., "Nanoparticle immunoagglutination Rayleigh scatter assay to complement microparticle immunoagglutination Mie scatter assay in a microfluidic device." 2011, Colloids and Surfaces B: Biointerfaces, pp. 168-173.
Kosaka et al., "Circulating microRNA in body fluid: a new potential biomarker for cancer diagnosis and prognosis." Oct. 2010, Cancer Sci., vol. 101, pp. 2087-2092.
Krishnan et al., "Alternating current electrokinetic separation and detection of DNA nanoparticles in high-conductance solutions." 2008, Electrophoresis, pp. 1765-1774.
Krishnan et al., "Rapid Isolation and Detection of Cell Free Circulating DNA and Other Disease Biomarkers Directly from Whole Blood." 2011, Circulating Nucleic Acids in Plasma and Serum, pp. 247-257. DOI: 10.1007/978-90-481-9382-0_34.
Kuo et al., "A microfabricated CE chip for DNA pre-concentration and separation utilizing a normally closed valve." 2009, Electrophoresis, pp. 3228-3235.
Linnarsson, Stan, "Magnetic sequencing," Nature Methods, vol. 9, No. 4, 339-341, Apr. 2012.
Ma et al., "Circulating microRNAs in cancer: origin, function and application." 2012, Journal of Experimental & Clinical Cancer Research, vol. 31.
Mallick et al., "MicroRNAs and lung cancer: Biology and applications in diagnosis and prognosis." Aug. 3, 2010, Carcinog, vol. 9.
Marshall et al., "Extraction of DNA from Malaria-Infected Erythrocytes Using Isotachophoresis." 2011, Analytical Chemistry, pp. 9715-9718.
McManus et al., "Circulating MicroRNAs in Cardiovascular Disease." Comment on Circulation. 124(18), Nov. 1, 2011, Comment on Circulation, pp. 1936-1944.
Mitchell et al., "Circulating microRNAs as stable blood-based markers for cancer detection." Jul. 29, 2008, PNAS, vol. 105, pp. 10513-10518.
Morales et al., "Continuous microfluidic DNA and protein trapping and concentration by balancing transverse electrokinetic forces." 2012, Lab Chip, pp. 99-108.
Qiao et al., "Wirelessly powered microfluidic dielectrophoresis devices using printable RF circuits." 2011, Lab Chip, vol. 11, pp. 1074-1080.
Qu et al., "Circulating miRNAs: Promising Biomarkers of Human Cancer." 2011, Asian Pacific Journal of Cancer Prevention, vol. 12, 2011, pp. 1117-1125.
Shaikh et al., "Collection, focusing, and metering of DNA in microchannels using addressable electrode arrays for portable low-power bioanalysis." 2005, PNAS, 2006, pp. 4825-4830.
Shopova et al., "Plasmonic enhancement of a whispering-gallery-mode biosensor for single nanoparticle detection." 2011, Applied Physics Letters, pp. 243104-243104-3.
Suzuki et al., "Characterization of circulating DNA in healthy human plasma." Sep. 3, 2007, Clinica Chimica Acta, vol. 387, pp. 55-58.
Tamkovich et al., "Circulating Nucleic Acids in Blood of Healthy Male and Female Donors." Nov. 2004, Clinical Chemistry, vol. 51, pp. 1317-1319.

(56) References Cited

OTHER PUBLICATIONS

Thery et al., "Isolation and Characterization of Exosomes from Cell Culture Supernatants." New York : John Wiley, 2006, Current Protocols in Cell Biology, pp. 3.22.1-29.
You et al., "Cell-phone-based measurement of TSH using Mie scatter optimized lateral flow assays." Biosensors and Bioelectronics, 2013, pp. 180-185.
Yu et al., "Circulating MicroRNAs: Potential Biomarkers for Cancer." 2011, Int. J. Mol. Sci., vol. 12, pp. 2055-2063.
Zhu et al., "Circulating microRNAs in breast cancer and healthy subjects." BioMed Central, 2009, vol. 2, p. 89.
International Search Report and Written Opinion of International Application No. PCT/US2014/011942; dated Apr. 15, 2014; 12 pages.
International Search Report and Written Opinion of International Application No. PCT/US2014/011909; dated Dec. 9, 2014; 15 pages.
Office Action for U.S. Appl. No. 14/761,603, filed Mar. 1, 2017; 29 pages.

\* cited by examiner

MICROFLUIDIC DEVICES TO EXTRACT, CONCENTRATE AND ISOLATE MOLECULES

CROSS REFERENCE TO RELATED APPLICATIONS

This patent document is a 35 USC § 371 National Stage application of International Application No. PCT/US2014/011909 filed Jan. 16, 2014, which further claims the benefit of priority of U.S. Provisional Patent Application No. 61/753,402, entitled "MICROFLUIDIC DEVICES TO EXTRACT, CONCENTRATE AND ISOLATE MOLECULES," filed on Jan. 16, 2013. The entire content of the aforementioned patent applications are incorporated by reference as part of the disclosure of this application.

TECHNICAL FIELD

This patent document relates to biological sensors and analytical devices.

BACKGROUND

A biological sensor or biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, aptamers, peptides, nucleic acids, etc., or small molecules such as carbohydrates, as well as virus and living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by a suitable transduction mechanism, for example, electrical, magnetic, mechanical, physicochemical, electrochemical, optical, piezoelectric, or others.

SUMMARY

Microfluidic techniques, systems, and devices are disclosed for efficiently extracting, capturing, concentrating, and isolating molecules (e.g., such as nucleic acids such as DNA and RNA substances, including microRNAs or "miRNAs") from whole blood and biological fluids using electrophoretic effects.

In one aspect, a device to capture molecules from a fluid includes a substrate formed of a material that is electrically insulating, a microfluidic channel made of an electrically insulating material formed on the substrate to carry a bio-fluid containing molecules including nucleic acids, an array of electrodes formed on the surface along a parallel direction of the microfluidic channel constituting a capture region, in which the array of electrodes are operable to produce an electric field across the microfluidic channel that creates an electrostatic attractive force on the nucleic acids to immobilize them in the capture region, and a chamber formed on the substrate of the electrically insulating material and connected to the microfluidic channel, the chamber configured to have a volume less than that of the microfluidic channel and to collect nucleic acids that are released from immobilization in the capture region.

In another aspect, a device to capture molecules from a fluid includes a substrate formed of a material that is electrically insulating, a microfluidic channel made of an electrically insulating material and formed on the substrate to carry an electrolytic fluid containing biomolecules including nucleic acids and charged particles configured to bind the nucleic acids to a charged surface, a first chamber region formed in the microfluidic channel, the first chamber region structured to receive the electrolytic fluid containing the nucleic acids attached to the charged particles, a second chamber region in the microfluidic channel connected to the first chamber region and including one or more outlets to remove at least some of the electrolytic fluid, in which the second chamber region is configured to have a volume less than that of the first chamber region, and a filter region in the microfluidic channel between the first chamber region and the second chamber region and structured to include holes of a size preventing the particles to pass but allowing the nucleic acids to pass through to the second chamber region, such that, when the nucleic acids are released from attachment to the charged particles in the filer region, the released nucleic acids are collected in the second chamber region.

In another aspect, a device to capture molecules from a fluid includes a substrate formed of a material that is electrically insulating, a microfluidic channel made of an electrically insulating material and formed on the substrate to carry an electrolytic fluid containing biomolecules including nucleic acids, a first chamber formed in the microfluidic channel and structured to include two or more regions separated by a porous membrane pre-coated with charged particles configured to bind the nucleic acids to a charged surface, in which the porous membrane includes a plurality of holes of a size greater than that of the nucleic acids to allow them to pass through the porous membrane and smaller than the charged particles to prevent them to pass through the porous membrane, a second chamber in the microfluidic channel connected to the first chamber and including one or more outlets to remove at least some of the electrolytic fluid, a first control valve positioned in the microfluidic between the first chamber and the second chamber to control the flow of the electrolytic fluid between the first and second chambers, and a second control valve positioned in the microfluidic between the second chamber and the one or more outlets to control the flow of the electrolytic fluid out of the device, such that, when the nucleic acids are released from attachment to the charged particles in the filer region, the released nucleic acids are collected in the second chamber region.

The subject matter described in this patent document can be implemented in specific ways that provide one or more of the following features. The disclosed lab-on-a-chip devices, systems, and methods can be used to extract, concentrate, and detect specific biomolecules from fluids including biological fluids. In some implementations, for example, exemplary microfluidic devices of the disclosed technology can extract, concentrate, and detect miRNA markers from biofluids on the chip without PCR or sequencing. The disclosed microfluidic lab-on-a-chip devices, systems, and methods are highly sensitive, low cost, fast, minimally invasive, and applicable to all miRNA-based diagnosis, suitable for point-of-care applications. For example, the disclosed microfluidic techniques, systems, and devices provide the capability of high-efficiency capture of low abundance biomolecules including cell-free DNAs and RNAs with high throughput, e.g., 100× higher than conventional devices. In some exemplary applications, the disclosed technology can be implemented to capture and detect miRNAs, which can be used to provide early diagnosis of a wide range of diseases, e.g., including many types of cancers and heart diseases. In some aspects, the disclosed technology can function as the front-end extraction/enrichment component of any lab-on-a-chip miRNA diagnostic device or research tool. The disclosed technology can include a microfluidic platform for capture, release, and transport of biomolecules including nucleic acids into a small chamber to achieve orders of magnitude increase in concentration. In some embodiments, for example, an exemplary lab-on-a-chip device can contain three sections according to their functions, e.g., including a capturing section, releasing and recapturing section, and storage and/or detection section which houses the concentrated target molecules readily available for optical and/or electrical detection. In some implementations, for example, the exemplary devices can capture molecules via the electrostatic interactions between the molecules and the channel, e.g., harnessing intrinsic electric properties of DNAs and RNAs.

DETAILED DESCRIPTION

Figure 1A:
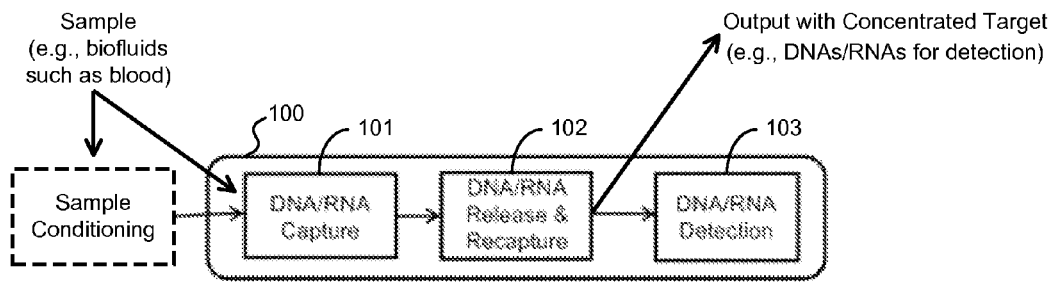
FIG. 1A shows a block diagram depicting the overall architecture and process flow of an exemplary microfluidic device of the disclosed technology.

Nucleic acids are polymeric biological molecules that are considered essential for all known forms of life. Nucleic acids include deoxyribonucleic acid (DNA) and ribonucleic acid (RNA), which are formed from particular arrangements of monomer subunit molecules called nucleotides. Nucleotides are composed of a nitrogenous base, a five-carbon sugar (e.g., deoxyribose if the polymeric biomolecule is DNA, or ribose if the polymeric biomolecule is RNA), and at least one phosphate group. There are many subtypes and chemical modifications of nucleic acids that serve one or more functions in the genetic make-up of living and non-living organisms.

For example, microRNAs (miRNAs) are small non-coding RNA molecules of about 21 to 23 nucleotides in length, which function in the regulation of gene expression. Over 2,000 types of mature miRNAs have been found to date, and new miRNAs continue to be discovered by research laboratories around the world. Because miRNAs are linked to over 100 diseases, including many types of cancers, they can be used as biomarkers for disease diagnosis. Furthermore, circulating miRNAs, either secreted by diseased tissues or produced due to immune responses, exist in blood and biofluids, so they are particularly promising for early disease diagnosis with minimal invasiveness.

Currently, any clinical miRNA detection technology using blood or biofluids face the challenge of very low concentrations of specific miRNAs and the time and cost of detection since accurate test results need to be produced fast and at low cost. For example, the level of specific miRNAs in blood or another biofluid such as saliva can be as low as 10 fM. For reliable detection of miRNAs or other biomolecules in practical settings, e.g., such as a point-of-care diagnosis, one may need to rapidly collect about 1-10 attomoles ($10^{-17-18}$ moles) of the target nucleic acids (e.g., miRNAs) from about 1 mL of blood. Under these exemplary conditions, to extract and concentrate enough amounts of miRNAs in less than 30 minutes, a flow rate of 30-100 µL/min would needed at decent collection efficiency (e.g., >10%), which is well beyond the capabilities of any existing/conventional microfluidic nucleic acid extraction devices. One alternative is to collect miRNAs encapsulated in exosomes, but the steps required to collect exosomes (e.g., ultra centrifuge at 100,000 gs or using CD63 antibody) can add extra time, cost and process complexity (e.g., 4-5 hours for 5-25% exosome collection efficiency). Therefore, free miRNAs directly from blood or biofluids can be chosen to be collected.

Many technical challenges exist to measure miRNAs and other nucleic acids present in biological fluids. For example, some miRNAs differ from each other by one or a few nucleotides, and the presence and concentration of the particular miRNA in a biofluid sample can be link to levels of various disease conditions. Based on the intense research efforts and fast progress in connecting miRNAs to specific diseases, e.g., particularly with circulating miRNAs, there is a strong belief in the medical community that miRNAs will become important biomarkers, in addition to proteins and DNAs, for diagnosis of a large number of diseases including, e.g., cancers, chronic diseases, immune diseases, etc. However, the medical community lacks devices for miRNA-based assays that are suitable for clinical applications, e.g., which can create a major bottleneck to translate the fast discoveries of miRNAs in the laboratories to the clinics.

There are many technical challenges to sense low concentrations of target biomolecules (e.g., like miRNA) against a background of high concentration of other biomolecules within physiologically relevant fluids. One way of achieving effective sensing includes preconcentrating the target biomolecules in the proximity of a sensor to increase the local concentration.

Microfluidic techniques, systems, and devices are disclosed for efficiently extracting, capturing, concentrating, and/or isolating molecules such as nucleic acids (e.g., including single stranded DNA and RNA substances, including miRNAs) from biological fluids, e.g., including whole blood. In some implementations, the disclosed microfluidic techniques, systems, and devices further include detecting the enriched and/or isolated molecules.

In some aspects, methods and devices to extract and concentrate circulating nucleic acids for in vitro diagnosis are described. Thus, the disclosed microfluidic techniques, systems, and devices can pertain to the field of lab-on-a-chip nucleic acid extraction and enrichment from blood and biofluids. Also, for example, for in vitro biomolecular diagnosis with minimum invasiveness, the disclosed microfluidic techniques, systems, and devices can detect the presence and abundance level of specific nucleic acids from blood and biofluids (e.g., saliva, sputum, urine, etc.) from patients. Many kinds of nucleic acids are present in the blood and biofluids and they are promising candidates as disease markers for diagnosis and prognosis of heart, lung, liver, central nerve system, chronic and infectious diseases, as well as cancer. Although PCR has been the gold standard for nucleic acid detection and deep sequencing has produced extremely rich information about person's health, PCR and deep sequencing cannot meet the cost and time requirements for clinical applications. The high equipment and reagent costs, as well as complicated operation and sample preparation steps, make these techniques unsuitable for point-of-care clinics, which is the global trend for future diagnostics.

For circulating nucleic acid assays, the concentrations of the biomarkers of interest are usually very low. For example, the DNA and RNA markers in patient's blood are several orders of magnitude lower than the molecules found in the tumors or damaged tissues. For many circulating miRNAs, their concentrations in the blood can be as low as femtomolars (fM). One fM represents about 1 million copies per milliliter of sample, which is below the sensitivity of today's molecular detection techniques, thus making PCR that increases the copy number of target DNA/RNA the only reliable method of detection in most cases. To eliminate the PCR process in clinics, the concentration of the target molecules should be increased. The disclosed technology includes microfluidic devices to concentrate circulating nucleic acids from blood and biofluids.

Conventional microfluidic devices capable of isolating, concentrating, or capturing nucleic acids have shown to be ineffective and unsuitable for clinical applications of DNA/RNA detection. For example, to collect a sufficient amount of specific circulating RNAs (e.g., ~1-10 attomoles or in the order of 1 million copies of target RNAs) from serum for reliable detection, clinical studies show that one needs to collect RNAs from about 1 mL of blood due to its low concentration (e.g., ~10 fM). Conventional microfluidic device cannot operate at a sufficient enough or high enough flow rate, e.g., >30 μL/min, while achieving high nucleic acid collection efficiency. For example, many devices can only operate at a flow rate of <1 μL/min or stopped flow.

The disclosed microfluidic devices, systems, and techniques can extract target molecules as the fluid flows through a microfluidic channel. In some implementations, the molecules are captured through electric interactions between the molecules and the substrates. After the desired amount of sample flows through the device and a wash process, the captured molecules are released to the fluid and then carried to a small chamber (e.g., 10 nL to 100 nL). As an exemplary estimate, if the method collects 10% of targeted molecules from 1 mL of sample and then brought to a volume of 100 nL, the molecular concentration is enhanced by 1000 times, thus greatly facilitating molecular detection.

An overall device architecture using a microfluidic platform and techniques for capture, release, and transport of target molecules (e.g., nucleic acids including miRNA) into a small chamber is described to achieve orders of magnitude increase in concentration. In one aspect, a device contains three sections according to their functions, e.g., a capturing section, a recapturing and/or enriching section, and a storage and/or detection section which houses the concentrated target molecules readily available for electrical and/or optical detection, e.g., including binding with molecular probes for detection. In one exemplary embodiment, for example, the key mechanism of capturing is via the electrostatic interactions between the molecules (e.g., nucleic acids) and the substrate, e.g., taking advantage of the intrinsic electric properties of DNAs and RNAs. Such electrostatic interactions can occur between the exemplary nucleic acids and the electrodes formed on the surface of the microfluidic channel, or the surface charge of a substrate such as silica beads (or other negatively charged surfaces). To release the captured molecules, the attractive force is neutralized by changing the pH value, altering the electrolytes, or removing the applied electric-field.

FIG. 1A shows a block diagram depicting the overall architecture and process flow of an exemplary microfluidic device 100 of the disclosed technology. The microfluidic device 100 can be implemented for miRNA capture and detection using blood or other biofluids to produce sensitive and accurate results fast and at low cost, e.g., including capturing and detecting specific types of circulating miRNA in the blood or biofluid from very low concentrations (e.g., ~10 fM). The microfluidic device 100 can be configured as a lab-on-a-chip device structured to include three sections. The device 100 includes a first section 101 that captures molecules (e.g., including nucleic acids such as double- or single-stranded DNA or RNA including miRNA) from a fluidic sample introduced and flowed through the molecular capture section 101 at high flow rate (throughput). For example, in some implementations, the molecular capture section 101 can receive a raw sample (e.g., such as whole blood drawn directly from a patient), whereas in other examples, the molecular capture section 101 can receive the sample after a sample preparation or conditioning process. For example, the molecular capture section 101 can immobilize the target molecules in the first section of the device 100 and allow the fluid initially containing the target molecules to be removed, e.g., thereby separating and/or isolating the target molecules from the initial sample fluid. The immobilized target molecules can be released by the molecular capture section 101 for recapture in a second section 102 of the device 100. The device 100 includes a molecular release and recapture section 102 that recaptures the released captured miRNAs to achieve high dynamic range. For example, in some implementations, the molecular release and recapture section 102 is of a substantially smaller volume than that of the molecular capture section 101, thereby enabling enriching or increasing the concentration of the recaptured target molecules. The device 100 includes a third section for specific label-free miRNA detection with ultrahigh sensitivity. In some implementations, for example, the molecular detection section 103 can be the same section of the microfluidic device 100 as the molecular release and recapture section 102.

An exemplary method to use the microfluidic device 100 to capture and detect nucleic acids from blood can include the following processes. In some examples, standard procedures can be used to lyse the red blood cells and take the serum sample for sample conditioning. The serum sample is introduced to the microfluidic device 100 and enters the molecular capture section 101 at a high flow rate (e.g., greater than 30 µL/min). For example, large serum samples can be introduced into the microfluidic device 100, e.g., including 1 mL or greater. The target nucleic acids are initially captured in the section 101 and released and recaptured in the section 102 to achieve enhanced concentrations of the target nucleic acids for detection in the section 103 (e.g., without PCR amplification), as described.

Figure 1B:
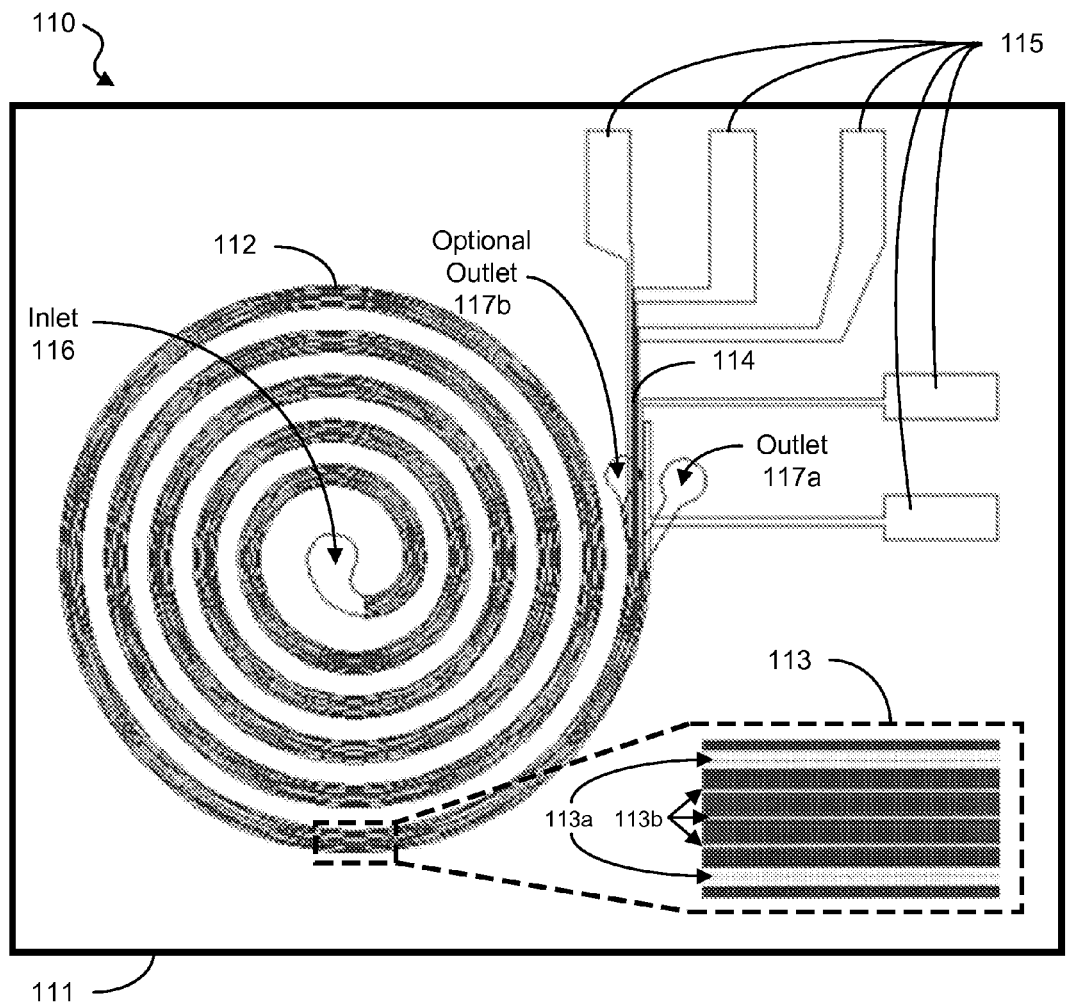
FIG. 1B shows a schematic illustration of an exemplary microfluidic device to capture, enrich, and/or detect target molecules from a fluid.

One exemplary embodiment of the device 100 is shown in FIG. 1B. FIG. 1B shows a schematic illustration of an exemplary device 110 to capture, enrich, and/or detect target molecules from a fluid. For example, the fluid can include biofluids including, e.g., blood, saliva, sputum, urine, vitreous fluid, and/or other fluid derived from an organism. The device 110 includes electric field assisted capture and release functionalities. In some implementations, for example, the device 110 can be used to capture nucleic acids (e.g., DNA or RNA, such as miRNA) contained in the blood that are at a concentration in a femtomolar range or less.

The device 110 includes a substrate 111 formed of a material that is electrically insulating. In some implementations, for example, the substrate 111 can be formed of glass, oxidized silica, cyclic olefin copolymer, polycarbonate, polyethylene, or other substrate including an electrically insulating coating or surface. The device 110 includes a microfluidic channel 112 made of an electrically insulating material (e.g., such as polydimethylsiloxane (PDMS)) formed on the substrate 111 to carry a fluid (e.g., biofluid) containing molecules, e.g., such as nucleic acids. The device 110 includes an array of electrodes 113 formed on a surface within the microfluidic channel 112 along a parallel direction of the microfluidic channel, e.g., constituting a capture region of the device 110. The array of electrodes 113 are operable to produce an electric field across the microfluidic channel 112 that can create an electrostatic attractive force on the molecules (e.g., nucleic acids) to immobilize them within the capture region of the device 110. The device 110 can include an inlet 116 to receive the fluid, e.g., which can be a raw sample or a conditioned sample. The device 110 can include one or more outlets 117 (e.g., depicted in FIG. 1B as outlet 117a and optional outlet 117b) for removing the sample fluid after flowing through the capture region. For example, a plurality of outlets 117 can be used to control the flow rate of the sample fluid through the device 110.

The device 110 includes a microchamber 114 formed on the substrate 111 at the end of the microfluidic channel 112 to receive the captured molecules after they are released from the capture region and recapture the released molecules, e.g., thereby constituting a recapture region of the device 110. For example, the microchamber 114 can be configured to have an area and/or volume substantially smaller than the microfluidic channel 112 to provide a section of the device to collect, enrich and increase the concentration of the captured molecules by the device 110. For example, in some implementations, the microfluidic channel 112 (capture region) can be configured to have a volume in the microliter range (e.g., ~5 µL), whereas the microchamber 114 can be configured to have a volume in the nanoliter range (e.g., ~10 to 100 nL). In some implementations, for example, the microchamber 114 provides a detection region of the device 110 for electrical and/or optical detection of the enriched recaptured molecules within the chamber 114. For example, in some implementations, the microchamber 114 can include molecular probes capable of binding the molecules in the chamber 114 for detection, e.g., via hybridization for examples when the target molecules are nucleic acids.

In some embodiments, for example, the device 110 can further include one or more detection regions or chambers 115 formed on the substrate 111 to provide an optical or electrical interrogation section to characterize (e.g., quantify) the presence, concentration, and/or properties of the captured molecules. In such embodiments, for example, characterization of the recaptured (and enriched) molecules can be implemented in the microchamber 114 (e.g., the microchamber 114 can serve as the detection region 115) as well as in the one or more detection regions 115.

For example, the immobilized molecules (e.g., nucleic acids) can be released from the capture region by implementing at least one of the following exemplary processes. In one exemplary process, the device 110 can be operated to remove or reduce the applied electric field (and thereby release the immobilized molecules from the capture region) while flowing another fluid to fluidically transfer the released molecules to the recapture region 114 of the device 110. In another exemplary process, the device 110 can be operated to receive a buffer fluid capable of changing the pH of the fluidic environment of the capture region, and thereby altering the attractive force of the applied electric field to release the release the immobilized molecules from the capture region.

In some implementations of the device 110, for example, the microfluidic channel 112 (in the capture region) can be configured as a spiral-shaped channel. For example, the exemplary spiral shaped microfluidic channel 112 can be configured to have a length of at least 40 cm and a diameter of 4 cm or less. In other implementations, for example, the microfluidic channel 112 can be configured as a straight channel in another geometry on the substrate 111. The exemplary embodiment shown in FIG. 1B depicts the spiral geometry of the capture region of the microfluidic device 110. The arrayed electrodes 113 are configured along the spiral-shaped channel 112. This exemplary embodiment can be configured to have a large effective channel length (e.g., of over 40 cm) in spite of its compact size (e.g., 4 cm diameter).

The inset of FIG. 1B shows a diagram of an exemplary configuration of the array of electrodes 113 of the device 110. In this example, the array of electrodes 113 includes two peripheral electrodes 113a and interior electrodes 113b arranged along the direction of the microfluidic channel 112. The peripheral electrodes 113a are arranged on the outlying portion of the channel surface and are structured to include a larger width (e.g., 300 µm to 1 mm) than interior electrodes 113b (e.g., which may range from 10 µm to 30 µm). In some examples, the electrodes of the array 113 can be configured of gold, platinum, or other metallic material having good electric conductivity and noncorrosive properties. In some implementations, the electrodes 113 can be functionalized to attach molecules or molecular structures, e.g., including targeting ligands to assist in binding the target molecules to the capture region of the microfluidic channel 112.

For example, the device 110 can use electrophoretic and/or dielectrophoretic forces to enable selective capturing of biomolecules in the capture region based on the characteristic frequency response of the dielectric permittivity of the biomolecule versus that of the medium. Dielectrophoresis (DEP) is an electrokinetic phenomenon in which a force is exerted on a dielectric particle (e.g., polarizable molecules and nanoscale particles) in an aqueous medium when the particle is subjected to a non-uniform electric field.

Dielectrophoresis can be used to attract and separate various particles in aqueous media, depending on the dielectric response of the particle in the presence of the non-uniform electric field. Although particles in general can exhibit dielectrophoretic activity in the presence of an electric field, the magnitude of the dielectrophoretic force depends on the type of medium, certain properties of specific particles, e.g., electrical properties and shape and size, and the frequency of the electric field exerted on the particles. For example, tuning the electric field to particular frequencies can manipulate particles with a degree of selectivity, e.g., which can result in orientation, transportation, and/or separation of the particles in the medium. For example, the non-uniform electric field can create regions within the medium of greater and lesser electric field magnitudes that can steer the particles. For example, when the permittivity of the medium is greater than that of the particle, the particle moves to regions of lesser electric field strength within the medium. Alternatively, for example, when the particle's permittivity exceeds that of the medium, the particle moves to regions of stronger electric field strength.

An external circuit or electrical supply source can be electrically coupled to the array of electrodes 113 to provide an electrical signal and power to the device 110. For example, in some implementations, a DC electrical potential can be applied across the peripheral electrodes 113a parallel along the microfluidic channel 112 to produce an DC electric field. For example, because the device 110 can be operated at a high flow rate (e.g., 30 µL/min or greater), the applied DC potential can be greater than the high threshold of hydrolysis of 0.82 $V_{DC}$ (e.g., 2 $V_{DC}$), as the applied electrical field would not damage the nucleic acids during implementation. In some implementations, for example, an AC electrical potential can be applied across the peripheral electrodes 113a parallel along the microfluidic channel 112 to produce an AC electric field. For example, the applied AC electric field may cause a negative dielectrophoretic (NDEP) effect in high electrolytic solutions to provide the molecular capture force of the exemplary nucleic acids in the capture region. In some implementations, for example, both an AC electric potential with a DC bias may be applied. In some configurations, for example, the interior electrodes 113b are not directly connected to an external circuit, and rather function to bend or shape the electric field produced by the applied electrical potential on the peripheral parallel electrodes 113a. Yet in some configurations, for example, each of the interior electrodes 113b can be connected to the external circuit so that their voltage value or waveform can be independently controlled and set.

In some implementations of the device 110, the exemplary biofluids is flowed through the microfluidic channel 112 at a flow rate of 30 µL/min or less. In some implementations of the device 110, for example, the substrate 111 can further include silica beads configured on the surface of the substrate 111 within the microfluidic channel 112, in which the silica beads provide a negative surface charge used to attract and bind the nucleic acids having a net positive charge. In other implementations of the device 110, for example, the substrate 111 can further include silica beads configured on the surface of the substrate 111 within the microfluidic channel 112, in which the silica beads provide a positive surface charge used to attract and bind the nucleic acids having a net negative charge.

Figure 1C:
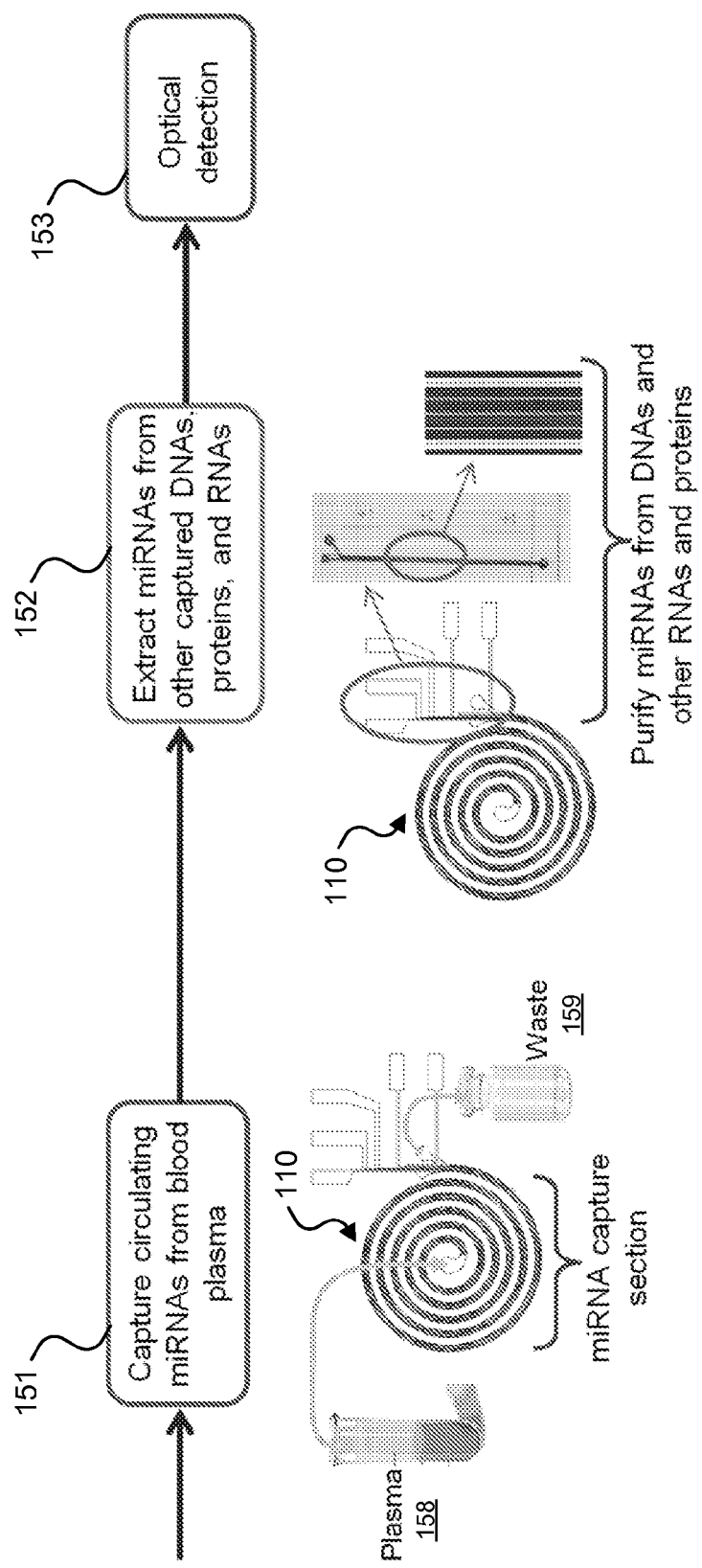
FIG. 1C shows an illustrative process flow diagram of an exemplary lab-on-a-chip device implemented to capture and extract miRNA molecules from blood plasma.

FIG. 1C shows an illustrative diagram of the process flow of the exemplary lab-on-a-chip device 110 implemented to capture and extract miRNA molecules from blood plasma. As shown in the diagram, a process 151 can be performed to capture circulating miRNAs from blood plasma or whole blood received by the device 110 (e.g., via the inlet 116) from a sample vial or container 158. In the flow direction of the blood plasma, the array of electrodes 113 formed in parallel with the microfluidic channel 112 are operated to electrophoretically capture miRNAs as they travel through the channel (shown in FIG. 2A). For example, since miRNAs carry negative charge (e.g., about 23 electron charge for a 20 nt miRNA that is about 7 nm long), they are attracted to the positive electrodes within the capture section of the device 110. Those captured miRNAs can be released from the capture section and recaptured in the microchamber 114 recapture section, e.g., having a much smaller volume than that of the capture section (e.g., 5 µL for the capture region as compared to 50 nL of the recapture region).

A process 152 can be performed to extract the miRNAs from other captured DNAs, proteins, and RNAs, etc., e.g., by purifying miRNAs from DNAs, RNAs, proteins and other biomolecules. For example, the recapture section controls the amount of miRNAs that can be released to the exemplary third section for detection (e.g., detection region 115), e.g., which can be implemented to detect multiple target miRNAs to assure linear response and high dynamic range, a desired feature for miRNAs of widely varying concentrations. For example, in some implementations, the microchamber 114 can be configured to include one or more electrodes (e.g., such as in the array of electrodes 113), which can be operated to produce an electric field in the microchamber 114 to create an electrostatic attractive force on the released miRNAs transferred to the microchamber 114 to recapture them within the recapture region of the device 110. The process 152 can be implemented to apply an electric field to capture the miRNAs from the other types of nucleic acids, proteins, and other biomolecules based on the parameters of the applied electric field and properties of the miRNAs (e.g., zeta potential) that would cause capture of only the miRNAs.

In some implementations, for example, molecular probes can be functionalized to the surface of the substrate 111 in the recapture section 114 for assistance in optical detection and characterization of the recaptured miRNAs. For example, the molecular probes can be configured to have complimentary base pairs specific to the target miRNA, and thereby hybridize only with the target miRNAs recaptured in the recapture section 114. In other implementations, for example, the detection region 115 can be modified to include the molecular probes on the surface of the substrate 111 in that region, where the extracted miRNAs can be transferred to the detection region 115 such that they bind (e.g., hybridize) to the molecular probes having complimentary base pairs specific to the target miRNA. A process 153 can be performed to use optical or electrical characterization schemes to detect specific binding events of target miRNAs.

For example, in some implementations using the exemplary device 110 including the detection region 115 for the capture of a sufficient amount of miRNAs with high throughput (flow rate) for particular applications, the capture section can be configured to be long and contain a total volume in the microliter range, e.g., around 5 µL. Yet, in spite of the high capture efficiency, for example, the miRNA concentration may still be relatively low for certain applications, and/or there may be a mismatch between the volume of the capture region 112 (e.g., ~5 µL) and the volume of the exemplary detection region 115 (e.g., ~100 nL). Therefore, the microchamber 114 can serve as an interface section that (i.) recaptures all miRNAs released from the capture region 112, (ii.) has a volume more closely comparable to the detection region 115, and (iii.) can introduce any desired amount of miRNAs to the detection region 115. The exemplary interface section can use the same electrophoretic effects to recapture the miRNAs released from the capture region 112 but at a much lower flow rate (e.g., 500 nL/min), e.g., since only 5 μL of fluid through may be needed to be moved. Also, for example, by controlling the duty cycle (e.g., from 0% to 100%) of the voltage when the miRNAs are moved into the detection region 115, digital control of the amount of miRNAs that enters the detection area for binding with the molecular probes can be implemented. Here, for example, 0% duty cycle (e.g., voltage off) allows all miRNAs to enter the detection area, and 100% duty cycle (e.g., voltage on all the time) allows no miRNAs to enter the detection area. In this manner, for example, the exemplary device 110 can possess high dynamic range and operate in the linear response regime.

Exemplary fluidic dynamics simulations and implementations were performed that demonstrate the design, fabrication, and characterization of exemplary lab-on-a chip devices of the disclosed technology to capture miRNAs from blood samples. In some examples, the effects of electrophoresis and microfluidics are used to capture miRNAs at high throughput and efficiency and release them into the detection area in a controlled manner.

The exemplary implementations of the microfluidic device 110 illustrated in FIG. 1B were performed which included applying an electric potential on the array of parallel electrodes at 2 V bias. The exemplary results of the implementations provided over 30% DNA/RNA collection efficiency achieved at a flow rate as high as 30 μL/min, e.g., resulting in an operation time of 30 minutes to collect over 1 attomole of specific RNAs in a spiked sample (as shown and discussed later in FIG. 2B). These exemplary results demonstrate that the exemplary device design has the capability of collecting a sufficient amount of RNAs in conditions compatible with the clinical setting.

Figure 2A:
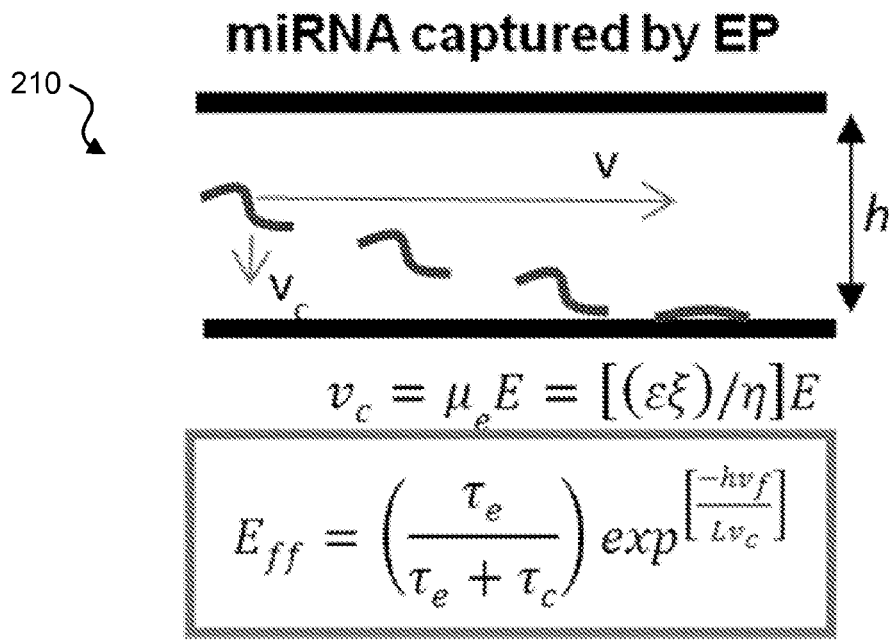
FIG. 2A shows a diagram of the exemplary capture section of the exemplary microfluidic device in FIG. 1B.

FIG. 2A shows a diagram 210 of the principle of molecular capture (e.g., such as miRNAs) by electrophoresis in the capture section (e.g., the exemplary spiral configuration of the microfluidic channel 112) of the device 110 illustrated in FIG. 1B. The capture efficiency ($E_{ff}$) is represented in Eq. (1), indicating an exponential dependence of the capture efficiency on channel length (L), among other factors.

$$E_{ff} = \left(\frac{\tau_e}{\tau_e + \tau_c}\right) \exp\left[\frac{-hv_f}{Lv_c}\right] \rightarrow \frac{\tau_e}{\tau_e + \tau_c} \text{ when } \frac{hv_f}{Lv_c} \ll 1 \quad (1)$$

where $\tau_c$, $\tau_e$ are the RNA (DNA) capture and escape time, and h, L are the channel height and channel length, respectively.

For example, the exemplary design of the device 110 (e.g., including the array of electrodes 113 in parallel with the microfluidic channel 112) can optimize the DNA/RNA capture efficiency at high flow rate to extract enough amounts (e.g., ~1-10 attomoles or close to $10^6$ copies) of target DNA/RNA from milliliters of blood in a relatively short (e.g., <30 minutes) time period. The electric-field-assisted capture efficiency for DNAs and RNAs is closely related to the velocity ratio: $v_f/v_c$ where $v_f$ is the average flow velocity and $v_c$ is the travel velocity toward the capturing electrodes due to the electrophoretic (EP) effect. For example, the RNA capture velocity can be represented by $v_c = \mu_e E_c$, where $\mu_e$ is the mobility of RNA and $E_c$ is the magnitude of E-field in the capturing direction. For example, the mobility of short chain DNA or RNA $\mu_e = (\in \xi)/\eta$ (e.g., where $\in$, $\eta$, and $\xi$ are the dielectric constant, viscosity, and zeta potential, respectively) has a typical value of around $4 \times 10^{-4}$ cm$^2$/V-s. If the captured DNAs/RNAs do not escape due to the shear stress of the flow, the capture efficiency can reach 100% if the channel length is sufficiently long. The escape rate can be considered for the captured RNAs (DNAs) at high flow speed. As a result, the final RNA (DNA) capture efficiency, $E_{ff}$, can be represented as shown in Eq. (1) above. The data plot in FIG. 2B shows the flow rate dependence of the RNA extraction efficiency on the sample flow rate.

Figure 2B:
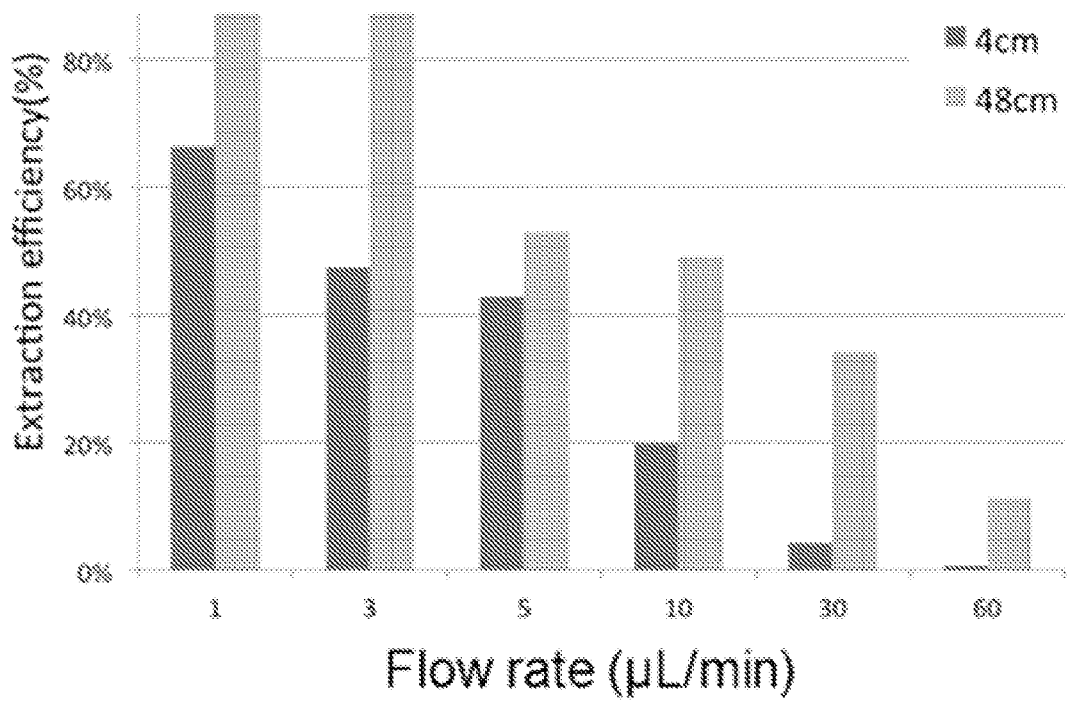
FIG. 2B shows a data plot of exemplary results of RNA capture efficiency of the exemplary microfluidic device in FIG. 1B.

FIG. 2B shows a data plot showing exemplary results of RNA capture efficiency for 4 cm and 48 cm long devices. The 48 cm channel has a spiral shape to maximize the space utilization (e.g., die size: 4 cm diameter).

Figure 2C:
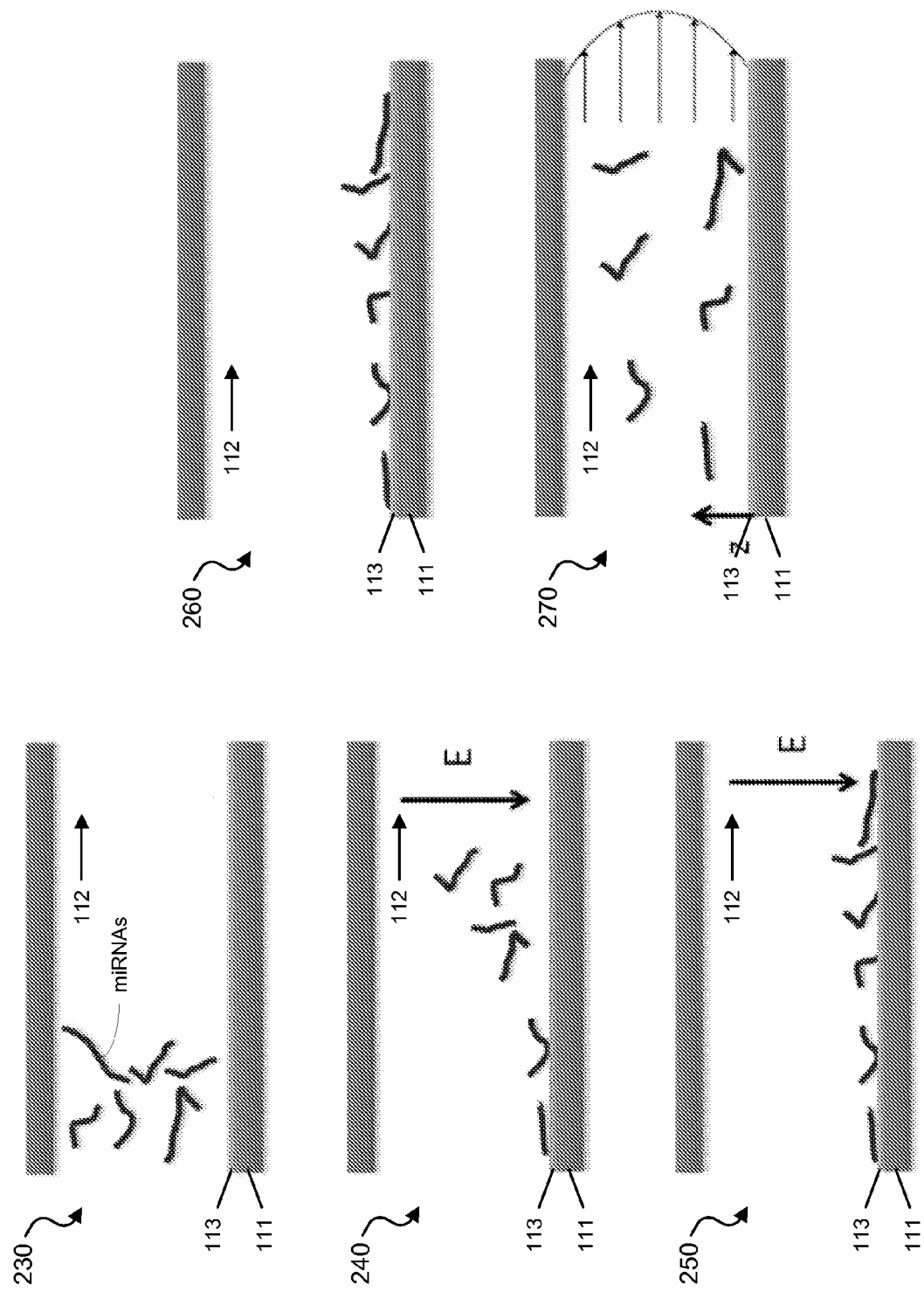
FIG. 2C shows a series of schematic diagrams illustrating the capture and elution for extracting miRNAs from a biofluid in the microfluidic channel of the exemplary microfluidic device in FIG. 1B.

FIG. 2C shows a series of schematic diagrams illustrating the capture and elution for extracting miRNAs from a biofluid in the microfluidic channel 112 of the exemplary device 110. Diagram 230 of FIG. 2C depicts an exemplary scenario in which miRNA contained in biofluid is injected into the microfluidic channel 112 (direction of flow depicted by the arrow). Diagram 240 of FIG. 2C of FIG. 2C depicts an exemplary scenario in which the miRNAs are subjected to an electrical field, e.g., where the negatively charged miRNAs are electrophoretically forced towards and captured by the array of parallel electrodes 113 on the substrate 111. For example, the electric field can produce an electrostatic attractive force on the miRNAs, e.g., which can depends of the Debye length, the charged density of the particles (e.g., miRNA), and the surface change density of the electrode surface. Van der Waals can also assist in driving the miRNAs to the surface of the microfluidic channel 112, e.g., when the particles are close to the electrodes. Diagram 250 of FIG. 2C depicts an exemplary scenario in which most or all of the miRNAs are trapped by the electrodes 113 as the biofluid flows out from the outlet at the end of the microfluidic channel 112. Diagram 260 of FIG. 2C depicts an exemplary scenario in which the captured miRNAs are released into the fluid. For example, the electrical power can be turned off to cause elution. Diagram 270 of FIG. 2C depicts an exemplary scenario in which the shear stress resulted from the parabolic flow velocity profile releases miRNAs from the substrate. For example, $$\frac{\partial C(z)}{\partial t} = D\frac{\partial^2 C(z)}{\partial C(z)^2} - \frac{\partial}{\partial z}(F(z)C(z))$$

is the equation for diffusion with external force. The shear stress at the wall of the channel can depend on the dynamic viscosity and the velocity gradient, e.g., $$\tau(z=0) = \eta\frac{\partial v}{\partial z}\bigg|_{z=0}.$$

The parabolic flow can be described by $$v(z) = 2V_{avg}\left(1 - \frac{(z-R)^2}{R^2}\right),$$

where R is the radius of the channel, z is the distance from the substrate.

Figure 2D:
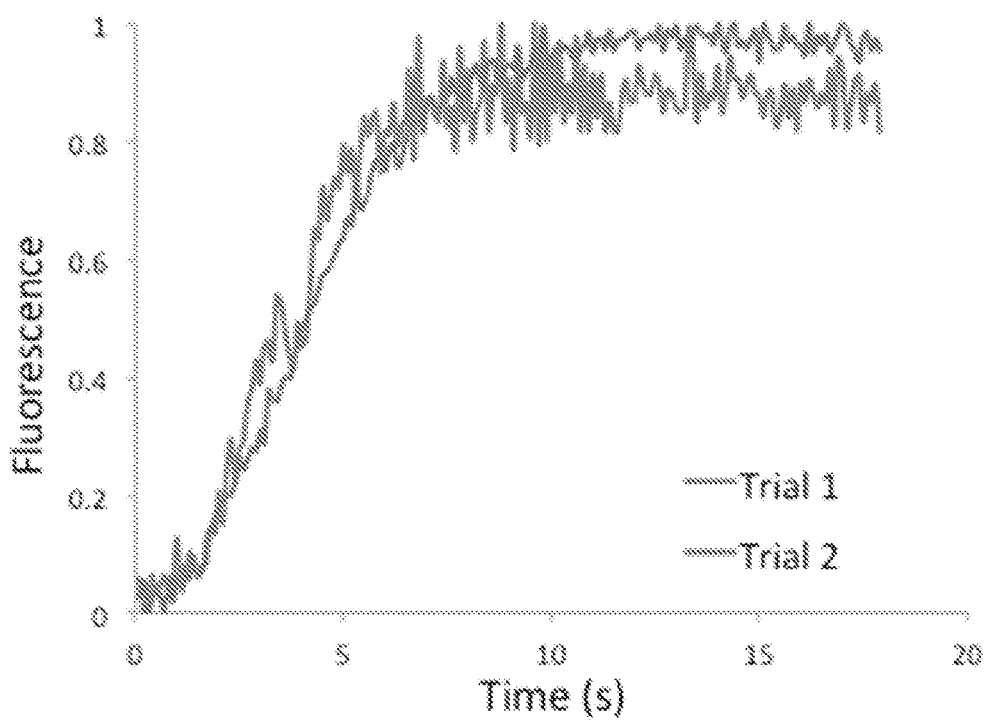
FIGS. 2D and 2E show data plots depicting exemplary results from exemplary implementations to measure the release time constant during release of nucleic acids from the capture region.
Figure 2E:
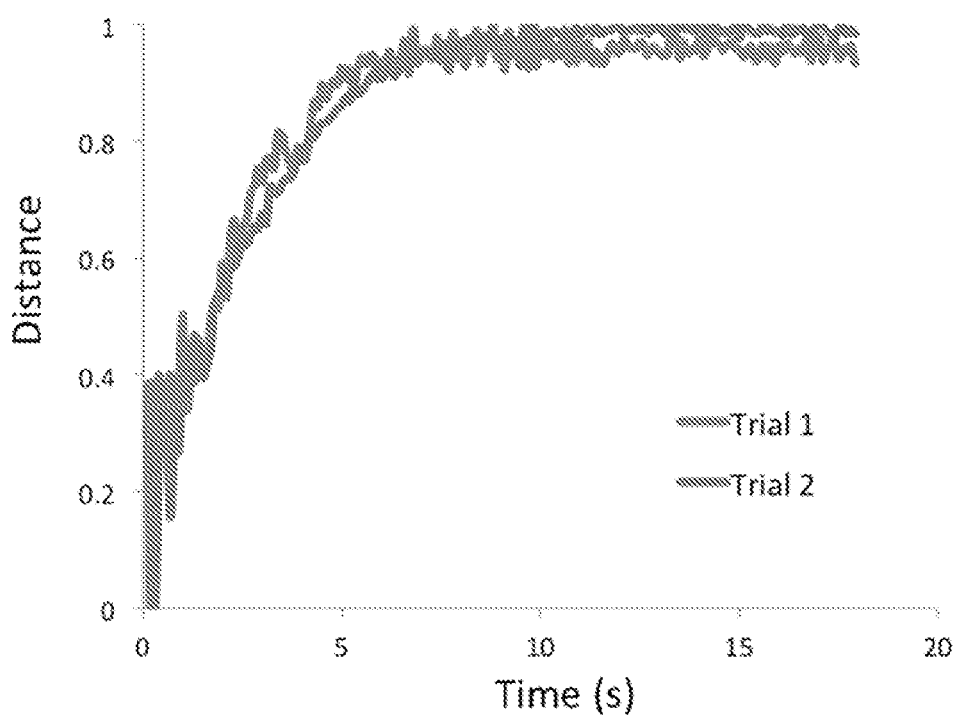

FIGS. 2D and 2E show data plots depicting exemplary results from exemplary implementations to measure the release time constant during release of nucleic acids from the capture region. FIG. 2D shows the fluorescence intensity as power is turned off at time zero. FIG. 2E shows the distance as power is turned off at time zero. As shown by the data plot in FIG. 2D, the fluorescent intensity increases as the DNAs move away from the electrode. Based on the Förster resonance energy transfer between a particle and a bulk media, the distant is proportional to the one third power of fluorescent intensity (e.g., $\sim F^{1/3}$). For example, the curve was fit with exponential function, and the release time constant at no flow was determined to be, in this example, 2.2 sec.

Figure 3A:
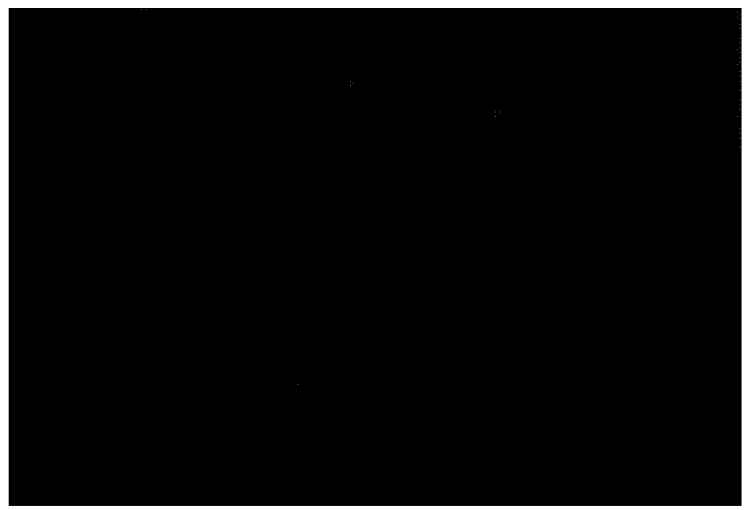
FIGS. 3A-3C show images of captured DNA molecules in the exemplary capture section of the exemplary microfluidic device of FIG. 1B.
Figure 3B:
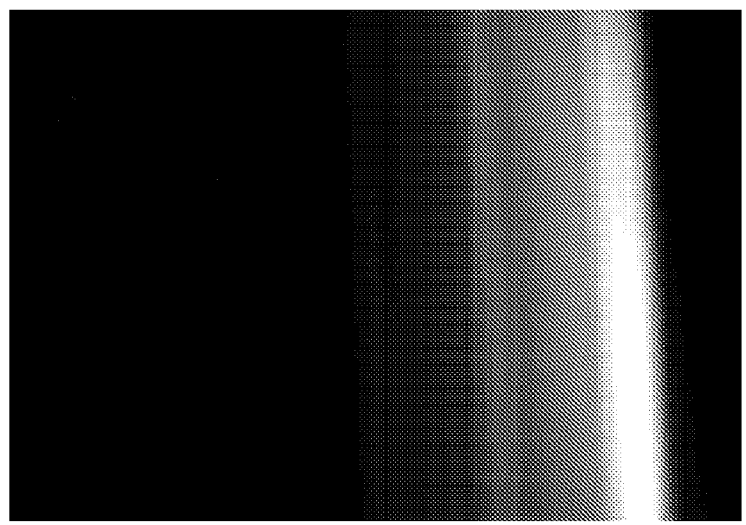
Figure 3C:
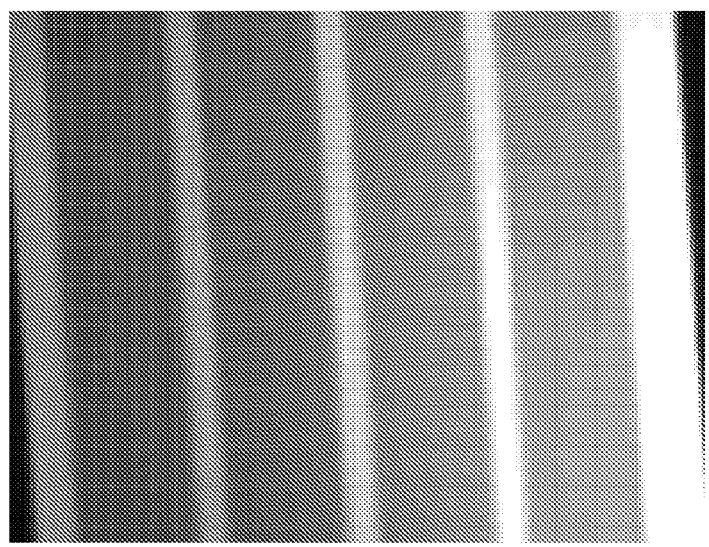

In some implementations, for example, after flowing through the desired amount of serum sample, the channel can be washed by RNAse-free buffer solution and the applied voltage can be turned off. The Brownian motions of RNAs and DNAs show the release of the captured molecules, as shown in FIGS. 3A-3C. FIG. 3A shows an image showing fluorescence of the captured DNAs is quenched by the applied E-field. FIG. 3B shows an image showing fluorescence recovers as the captured DNAs are gradually released after the E-field is turned off. FIG. 3C shows an image showing all captured DNAs are released after the applied E-field is turned off for 20 min.

To obtain the images shown in FIGS. 3A-3C, short length (e.g., about 20 base pairs) fluorescently labeled DNAs were used as an example to demonstrate the E-field assisted capture and release of circulating nucleic acids. When the DNAs are directed toward the positive electrodes and captured, the fluorescence is quenched due to the surface plasmonic coupling with the Au electrode, displaying dark areas near the DNA-capturing electrodes under fluorescence microscope. When the electric field is turned off, those captured DNAs are released. When the distance between DNAs and the electrode is greater than 10 nm, the surface plasmonic quenching effect disappears and the area shows much stronger fluorescence than the background. To assure maximum DNA/RNA release efficiency from the electrode, a thin layer of coating can be placed over the Au electrode. For example, the coating can be agarose gel, Streptavidin, BSA, etc.

In another aspect, microfluidic devices, systems, and techniques are described that use surface charged structures for electrostatic capturing and releasing of circulating nucleic acids within microfluidic channels and chambers. In some examples, the disclosed techniques can use surface charge of the substrate to achieve similar effects to the applied electric field for capturing and releasing molecules. Two exemplary advantages of this approach include simpler device fabrication and avoidance of generation of bubbles due to hydrolysis by the applied E-field. On the other hand, unlike the applied E-field present over the entire channel area, the surface charge is a very short range force defined by the Debye length (e.g., in the order of 1 nm). For example, the circulating nucleic acids "see" the surface charge of the substrate so they can be captured. In microfluidics, laminar flow is established and sample mixing is inefficient. Hence, the exemplary molecular capturing section 101 (of the exemplary device 100 shown in FIG. 1A) has a structure that gives strong effects of mixing to increase the chance of molecular capture.

Figure 4:
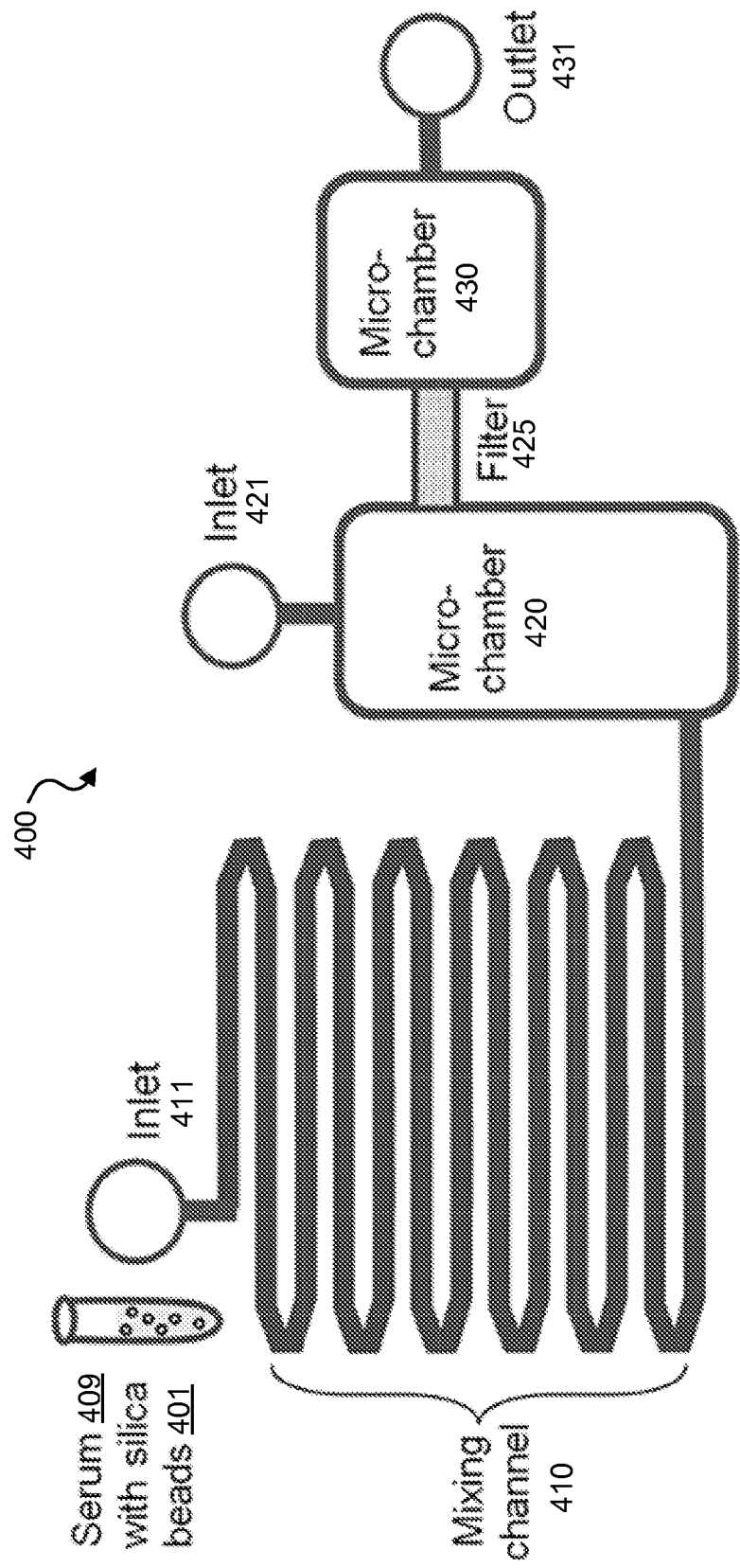
FIG. 4 shows a schematic of another exemplary microfluidic device for molecular capture and enrichment.

FIG. 4 shows a schematic of an exemplary microfluidic device 400 for molecular capture and enrichment, e.g., including DNA and/or RNA nucleic acids. The microfluidic device 400 includes a substrate formed of a material that is electrically insulating and a microfluidic channel made of an electrically insulating material and formed on the substrate to carry an electrolytic fluid 409 containing biomolecules including nucleic acids and negatively-charged or positively-charged particles 401 configured to bind the nucleic acids to the charged surface.

The device 400 includes a first microchamber 420 formed in the microfluidic channel, in which the first microchamber 420 is structured to receive the electrolytic fluid 409 containing the attached particles-nucleic acids. For example, the first microchamber 420 can be configured to have volume around 100 nL (e.g., 2 mm×2 mm×25 µm). The device 400 includes a second microchamber 430 in the microfluidic channel connected to the first microchamber 420, in which the second microchamber 430 is configured to have a volume substantially less than that of the first microchamber 420 and include one or more outlets 431 to remove at least some of the electrolytic fluid. The device 400 includes a filter region 425 in the microfluidic channel between the first microchamber 420 and the second microchamber 430, in which the filter region is structured to include holes of a size preventing the particles to pass but allowing the nucleic acids to pass through to the second chamber region. For example, when the nucleic acids are released from attachment to the charged particles in the filer region 425, the released nucleic acids are collected in the second microchamber 430, e.g., thereby enriching the concentration of the target nucleic acids.

For example, some biomolecules that are smaller than the size of the holes can pass through the filter region 425 to the second microchamber 430 and to the one or more outlets 431 for removal. In some implementations, for example, the filter region 425 can be formed of a hydrogel material having nano-scaled pores that block the particles having a micrometer-size. In some implementations, for example, the filter region 425 can be formed by flowing magnetic beads into the device 400 through the second inlet 421 coupled to the first microchamber 420 before receiving the electrolytic fluid 402, in which the magnetic beads are stopped by an external magnetic field applied at the position of the filter region 425. In some examples, the filter region 425 is capable of removal when the external magnetic field is removed. In some examples, the size of the holes of the filter region 425 is adjustable based on a quantity and size of the magnetic beads introduced through the second inlet 421.

There are several methods to implement the filter region 425 (e.g., microfilter). In one exemplary design, a hydrogel can be used as the filter since hydrogel has nanoscaled pores to let the fluid flow through but can block the micrometer sized beads. In another exemplary design, the filter can be created by first flowing larger magnetic beads into the device (e.g., from the inlet 421 connected to the first microchamber 420). These magnetic beads are stopped by an external magnetic field at the position of the filter 425. For example, this magnetic bead configuration of the filter region 425 can function as a 'dynamic filter" because the magnetic bead filter can be removed when the external magnetic field is removed. Also the properties of the magnetic bead filter can be adjusted by controlling the size and number of magnetic beads introduced from the inlet. These exemplary embodiments of the device 400 can be simple to fabricate since it does not require fabrication of a filter in the microfluidic device. In another exemplary approach, silica-coated magnetic beads can be used to capture the DNA/RNA and apply an external magnetic field to attract them to the second microchamber 430. In such exemplary designs, the filter may not be used.

In some implementations, for example, the microfluidic channel of the device 400 includes a mixing region 410 to facilitate mixing of the charged particles 401 and the target biomolecules (e.g., nucleic acids such as DNA and/or RNA, including miRNA) for attachment of the nucleic acids to the particles 401, e.g., based on electrostatic interactions in the electrolytic fluid. As shown in FIG. 4, the exemplary mixing region 410 of the microfluidic channel can be configured as a winding channel. The mixing region 410 can include an inlet 411 to receive the electrolytic fluid 409 into the microfluidic channel.

For example, the particles 401 having a negatively-charged or positively-charged surface can include silica beads. In some examples, the silica beads can be configured as silica-coated magnetic beads. For example, the attached silica-coated magnetic beads and nucleic acids can be captured in the first microchamber 420 by applying an external magnetic field.

In some implementations, for example, the electrolytic fluid 409 can be blood (e.g., serum sample shown in the schematic of FIG. 4) and be mixed with nano- or micro-scale structures having surface charge 401 (e.g., such as silica beads shown in the schematic of FIG. 4), which is introduced to the device 400 at an inlet 411 (as shown in FIG. 4). In other examples, the biofluid can include saliva, sputum, urine, vitreous fluid, or fluid derived from a living organism. For example, the nucleic acids contained in the blood are at a concentration in a femtomolar range. For example, the exemplary winding microfluidic channel structure of the exemplary mixing channel 410 can greatly enhance sample mixing and increase the 'rate of encounter' between the biomolecules (e.g., DNA and/or RNA) in the biofluid 409 and the silica beads 401. At the exit of the winding path of the exemplary mixing channel 410, for example, most RNAs and DNAs (e.g., including miRNAs) are attached to the silica beads 401 due to the electrostatic interactions in the electrolyte. In some implementations of the device 400, for example, the nano- or micro-structures having surface charge 401 can be configured as silica beads having negative surface charge. For example, the negative surface charge of the exemplary silica beads 401 can cause the DNAs and RNAs (e.g., including miRNAs), which also carry negative charge, to attract to the negatively charged beads 401 in electrolyte, e.g., due to the effect of "like-charge attract" that is understood in biophysics.

The exemplary DNA/RNA-attached beads can exit the winding channel and stay in the first microchamber 420, while the sample fluid containing other molecules (e.g., phospholipids, cholesterol, etc.) leaves the microchamber 420 through the filter 425 and is removed and/or collected from the outlet 431 of the second microchamber 430, e.g., as waste. For example, these exemplary DNA/RNA-attached beads can be kept in the first microchamber 420 because at the exit there is a microfilter that allows fluid to travel through but stops the pass of these beads.

For example, after the desired amount of serum (e.g., 0.5 to 1 mL) flows through the device 400 (e.g., removed from the outlet 431), in which the targeted nucleic acids (e.g., DNAs and/or RNAs, such as miRNA) are captured at the filter region 425 via the charged particles 401, the device 400 can be washed (e.g., with isopropanol) and a controlled amount of elusion buffer can be introduced from inlet 421 connected to the first microchamber 420 to release the captured DNAs and RNAs. After the release of the captured DNA/RNA from the charged particles 401 (e.g., silica beads, a negative pressure can be applied from the outlet 431 of the device 400 to suck the released DNA/RNA into the second microchamber 430, e.g., thereby separating the DNA/RNA from the charged particles (e.g., silica beads). In some implementations, for example, the second microchamber 430 can be configured to have a volume of 10-100 nL, in which it can contain all the circulating DNAs and RNAs extracted from the entire volume of serum (e.g., 1 mL). Hence the DNA/RNA concentration is enhanced by $10^3$ to $10^5$ times, in this example, making high sensitivity molecular detection feasible without PCR amplification. The DNA/RNA molecular detection can occur within the second microchamber 430 of the device 400 to minimize sample handling since extra sample handling causes sample loss and dilution.

In another aspect, microfluidic devices, systems, and techniques are disclosed for electrostatic capturing and releasing of circulating nucleic acids within microfluidic channels and multi-layered chambers using on-chip valve(s) and on-chip membrane filter(s).

Figure 5:
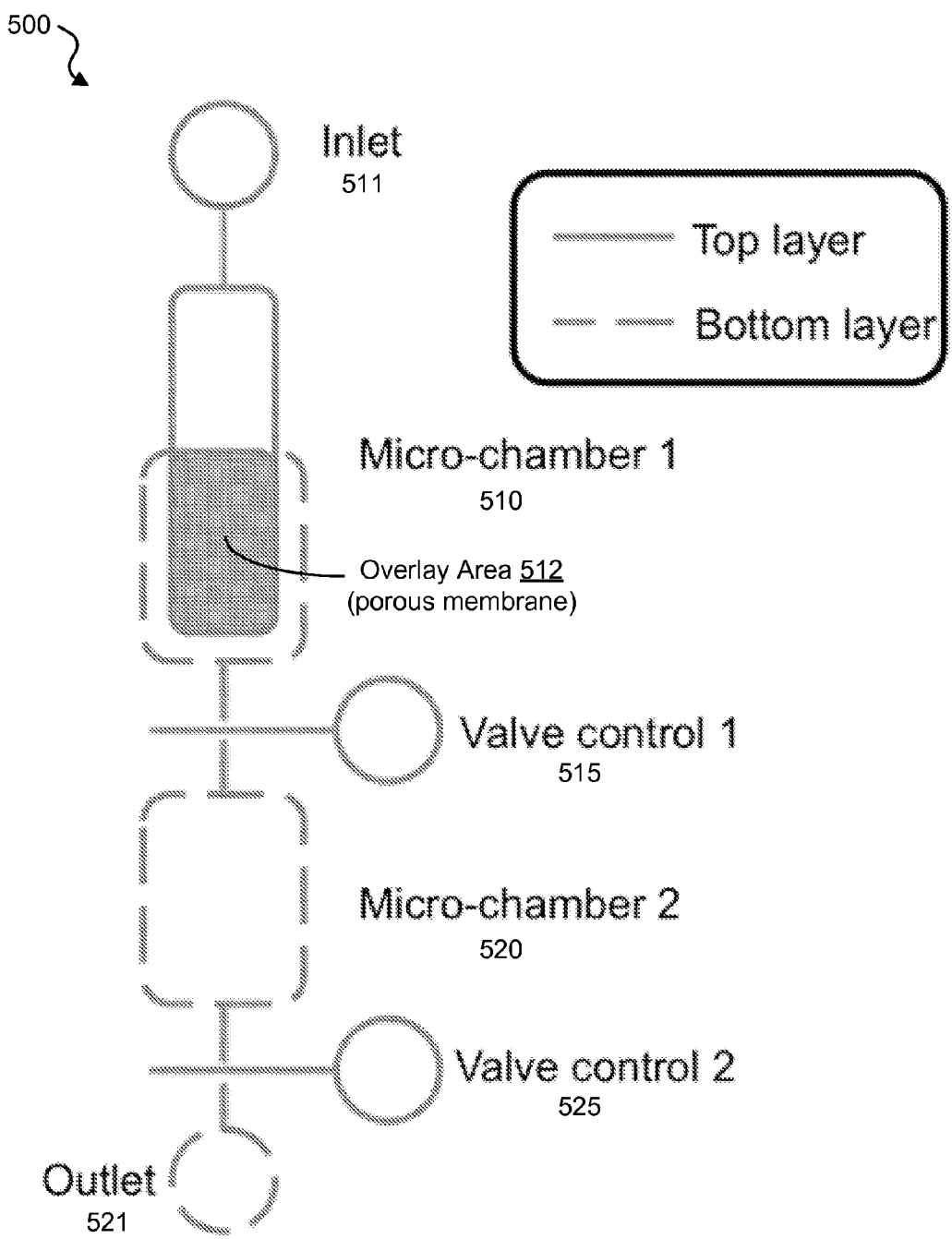
FIG. 5 shows a schematic of another exemplary microfluidic device with integrated on-chip valves and filter.

FIG. 5 shows a schematic of an exemplary microfluidic device 500 with integrated on-chip valves and one or more membrane filters. The device 500 includes a substrate formed of a material that is electrically insulating and a microfluidic channel made of an electrically insulating material and formed on the substrate to carry an electrolytic fluid containing biomolecules including nucleic acids. The device 500 includes a first microchamber 510 having a plurality of layers and formed in the microfluidic channel, in which the first microchamber 510 is structured to receive the electrolytic fluid containing the exemplary nucleic acids via an inlet 511 at one end of the microfluidic channel leading to the first microchamber 510. In some examples, the microfluidic channel is structured to include a top layer portion of the channel and a bottom layer portion of the channel within the first microchamber 510. For example, in the diagram of FIG. 5, an overlay area 512 of top layer portion and bottom layer portion in the first microchamber 510 is marked in gray color. In this exemplary embodiment, negatively-charged or positively-charged micro-scale structures 501 (e.g., silica microspheres) configured to bind the nucleic acids to their charged surface can be pre-packed in the overlay area 512 of the first microchamber 510 by a micro-porous membrane (e.g., 600 nm pores) that works as a filter to keep all the exemplary silica microspheres (e.g., 1 µm diameter) in the first microchamber 510 for DNA/RNA capturing. For example, the first microchamber 510 can be configured to have a small volume (e.g., in the nanoliters). The device 500 includes a second microchamber 520 formed in the microfluidic channel and connected to the first microchamber 510, in which the second microchamber 520 includes one or more outlets 531 to remove at least some of the electrolytic fluid. In some examples, the second microchamber 520 can be configured to have an even smaller volume less than that of the first microchamber 510. The device 500 includes a first valve 515 positioned in the microfluidic channel between the first and second microchambers 510 and 520 to control the flow of the fluid through the device 500 between these chambers. The device 500 includes a second valve 525 positioned in the microfluidic channel between the second microchamber 520 and the outlet 521 to control the flow of the fluid out of the device 500 from the second microchamber 520.

During DNA/RNA capturing phase, for example, both the first and second valves 515 and 525, respectively, are open, and the sample fluid passes the porous membrane in the overlay area 512 to be drained through the one or more outlet 531, except for the DNA/RNA that are captured in the first microchamber 510. After washing, for example, an elusion buffer can be introduced from the inlet 511 and fills the first microchamber 510 with the first valve 515 closed. After a sufficient period (e.g. 5 minutes) for the elution buffer to release the captured DNA/RNA, for example, the first valve 515 is opened and the second valve 525 is closed to move the released DNA/RNA to the second microchamber 520. In some implementations, for example, molecular probes may be immobilized to certain areas of microchamber 520 to allow hybridization with the target DNA/RNA for on-chip detection.

In existing bio-molecule purification kits, DNA/RNA are captured and eluted in cuvettes. The required volume of the DNA/RNA elution buffer is minimally 10 µL, e.g., in order to not sacrifice the capture efficiency. In contrast, in the integrated microfluidic device 500, for example, the tightly packed silica microspheres in the first microchamber 510 occupy a very small volume (e.g., ~10 nL) and the total volume of the elution buffer is precisely controlled by the exemplary on-chip valves 515 and 525. Therefore, for example, because of the extremely small dead volume, the required amount of elution buffer can be less than 100 nL. To process 1 mL sample (e.g., serum), the concentrations of DNA/RNA can be enriched by 1000-10,000 fold after elution.

For example, the device 500 can be implemented such that a biofluid sample is injected into the device 500 through the inlet 511 and captured by the silica microspheres while the fluid and other molecules flow through the layers of exemplary silica microspheres and the porous membrane to the remaining portions of the microfluidic channel leading to the outlet 521. After several washes, for example, the captured DNA/RNA are eluted and infused to the second microchamber 520 for detection.

The exemplary microfluidic device 500 uniquely uses a porous membrane in the microchannel as an on-chip filter. In some examples, track etched polycarbonate or polyester membranes can be included, e.g., because of the strictly controlled pore size and relatively straight pore structure. For example, when 1 µm silica microspheres are used to capture bio-molecules, the micro-porous membrane with an exemplary pore size between 0.6 µm and 0.8 µm in the first microchamber 510 can hold layers of closely packed microspheres. Exemplary advantages of the integrated microporous membrane can include, but are not limited to, (i) smooth surface to obtain waterproof sealing, (ii) negligible absorption and adsorption of filtrate, (iii) no particle shedding, (iv) precisely controlled pore size to stop microspheres while producing low enough flow resistance to allow high sample flow rate (e.g., 30 µL/min), (v) transparent or translucent membranes for optical observation/detection, and (vi) biologically inert.

The incorporation of the micro-porous membrane into the exemplary PDMS fluid chamber can be facilitated by depositing a 30 nm thick $SiO_2$ layer on both sides of the micro-porous (polycarbonate) membrane before bonding the membrane with the surface-treated PDMS. For example, since the on-chip filter uses a porous but less flexible membrane and the micro-valves use a highly flexible yet less porous membrane, a special design can be included to achieve process compatibility. Disclosed are fabrication process that can integrate both types of membranes in the microfluidic device, as illustrated in FIG. 6.

Figure 6:
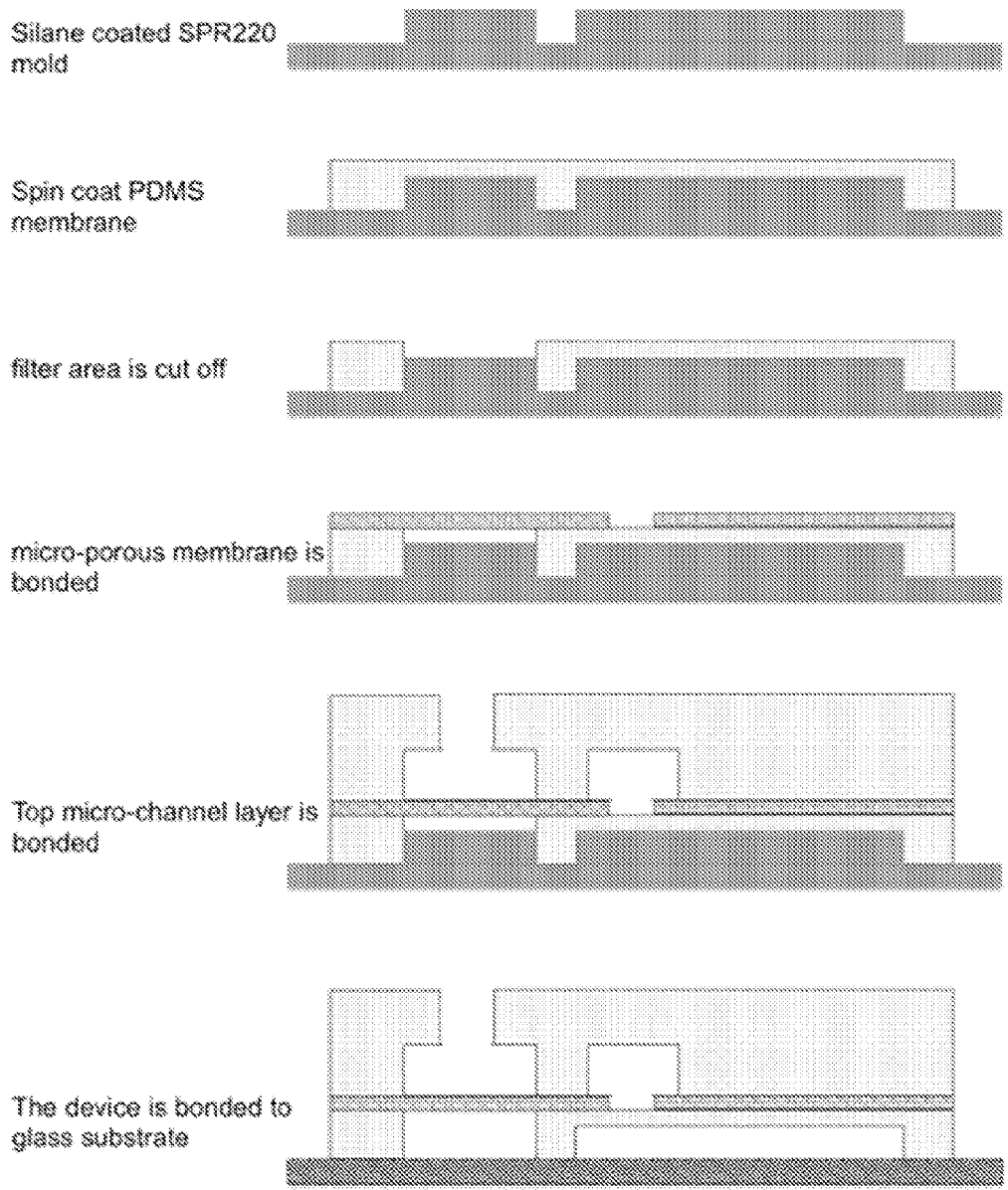
FIG. 6 shows a schematic illustration of an exemplary fabrication process of the exemplary microfluidic device with integrated filter and microvalves for biomolecule capture and enrichment.

FIG. 6 shows a schematic illustration of an exemplary fabrication process of the exemplary microfluidic device 500 with integrated filter and microvalves for biomolecule (e.g., DNA/RNA) capture and enrichment. For example, at first, the mold of the bottom microchannel layer is fabricated with photoresist (e.g., SPR-220 photoresist). For example, by heating the SPR-220 photoresist mold above its glass transition temperature to 200° C., the photoresist is reflowed to form a smooth pattern. PDMS can then be spin-coated onto the reflowed resist mold, e.g., after silane treatment to prevent PDMS adhesion during demolding. Next, a PDMS membrane is formed with the filter area removed using a cutting tool. Separately, a micro-porous membrane, e.g., after the coating of both sides of the surface with a 30 nm layer of $SiO_2$, is formed with the microvalve areas removed. The micro-porous membrane is bonded on the PDMS membrane. Subsequently, a top portion of the microchannel is formed based on the mold of the top microchannel layer using techniques previously described. The formed top portion microchannel layer is bonded to the top surface of the micro-porous membrane bonded above the bottom portion microchannel layer over its exemplary silane coated mold. The exemplary mold is removed from the bottom portion microchannel layer, and the microchannel layers with the bonded micro-porous membrane are bonded to a glass substrate.

Exemplary implementations using the device 500 to capture, enrich, and detect miRNAs were performed. For example, among the over 2,000 types of mature miRNAs known, some 88 miRNAs have been reported to show different expression levels in non-small cell lung cancer (NSCLC) patients. Moreover, for example, the combination of three circulating miRNAs (e.g., miR-155, miR-197, and miR-182) are quite unique to NSCLC. The disclosed lab-on-a-chip technology platform can be implemented for miRNA detection suitable for clinical applications, including capture, enrichment, detection, and characterization of miR-155, miR-182 and miR-197 for NSCLC clinical applications.

Figure 7:
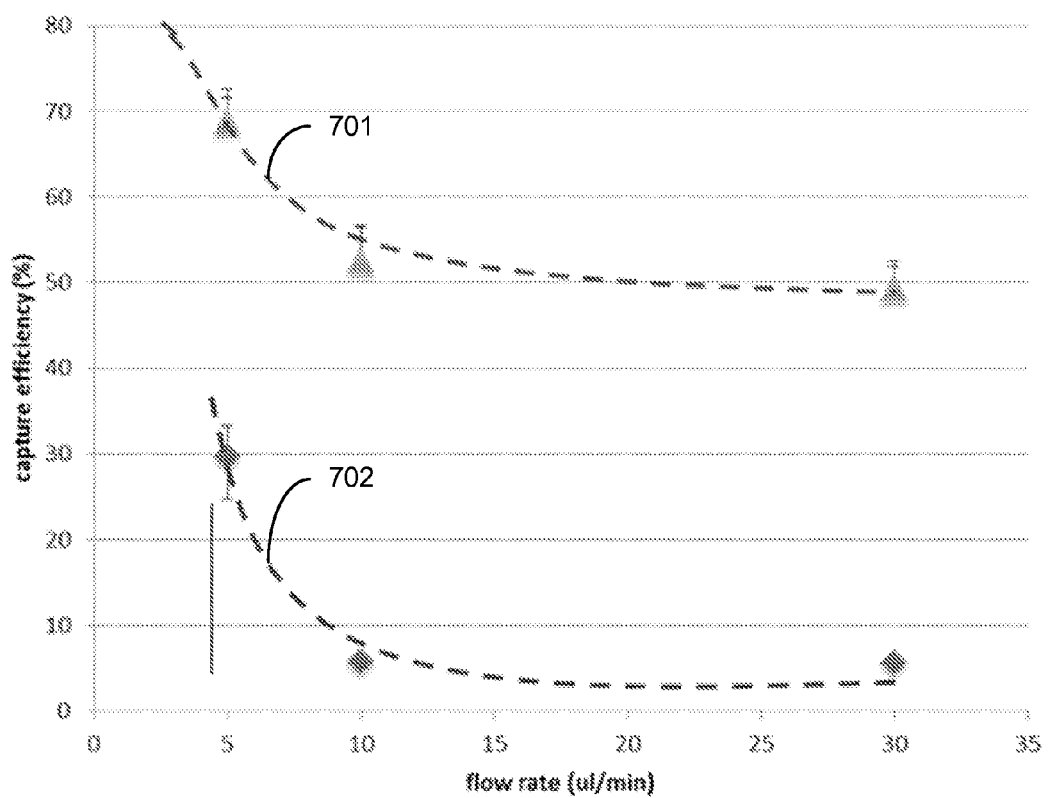
FIG. 7 shows a data plot showing the miRNA capture efficiency of the exemplary device under different sample flow rates.

FIG. 7 shows a data plot showing the miRNA (e.g., miR139) capture efficiency of the exemplary device 500 (e.g., fabricated following the process described in FIG. 6) under different sample flow rates. The upper (green) data curve 701 represents the capture efficiency over time in the presence of an average of three layers of 1 µm diameter silica beads stopped by the porous membrane. The lower (blue) data curve 702 represents the capture efficiency over time in the presence of a single layer of 1 µm diameter silica beads stopped by the porous membrane. As shown in the data plot, a larger number of silica beads provide a greater chance of contact between the nucleic acids and the surface of the beads via electrostatic interactions, thus yielding a greater nucleic acid capturing efficiency. However, it is noted for example, that when the layer of silica beads is too thick, the flow resistance increases substantially, limiting the flow rate of the sample and increasing the time of test. A good figure of merit can be defined as the product of the capture efficiency and the flow rate. From the exemplary data shown in FIG. 7, it appears that the device reaches the highest figure of merit with three layers of silica beads at a flow rate of 30 µL/min.

Methods, systems, and devices to extract and concentrate nucleic acids circulating in the blood and biofluids using microfluidic devices are described. For DNA and RNA biomarkers of very low concentration, this is a necessary step for clinical diagnosis to save the expensive and time consuming PCR amplification process. Exemplary devices include modules/sections to capture and release DNAs and RNAs to enhance the concentration of target molecules. The disclosed technology addresses the most serious bottleneck that has plagued microfluidic devices trying to achieve the similar purpose with only limited success, e.g., low sample flow rate. The exemplary devices can collect the target nucleic acids from the required amount of blood or biofluids (e.g., 1 to 10 mL) in a much shorter time (e.g., 30 minutes) an at high collection efficiency. Exemplary implementations using exemplary devices of the disclosed technology comparing sample flow rate and collection efficiency as a figure of merit establishes that the disclosed technology outperforms the existing devices by an estimate of 1000%.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A device to capture molecules from a biofluid, comprising:
   a substrate formed of a material that is electrically insulating;
   a microfluidic channel made of an electrically insulating material formed on the substrate to carry a biofluid containing molecules including nucleic acids;
   an array of electrodes formed on the surface along a parallel direction of the microfluidic channel constituting a capture region, wherein the array of electrodes are operable to produce an electric field across the microfluidic channel that creates an electrostatic attractive force on the nucleic acids to immobilize them in the capture region; and
   a chamber formed on the substrate of the electrically insulating material and connected to the microfluidic channel, the chamber configured to have a volume less than that of the microfluidic channel and to collect nucleic acids that are released from immobilization in the capture region,
   wherein the chamber is structured to include one or more electrodes operable to produce an electric field that creates an electrostatic attractive force on the nucleic acids to recapture them in the chamber.

2. The device of claim 1, wherein the biofluid includes at least one of blood, saliva, sputum, urine, vitreous fluid, or fluid derived from a living organism.

3. The device of claim 2, wherein the nucleic acids contained in the blood are at a concentration in a femtomolar (fM) range.

4. The device of claim 1, wherein the nucleic acids include at least one of DNA or miRNA.

5. The device of claim 1, wherein the device is configured to flow the biofluid through the microfluidic channel at a flow rate of 30 μL/min or less.

6. The device of claim 1, wherein the substrate further includes silica beads configured on the outer surface to provide negative surface charge used to attract and bind the nucleic acids.

7. The device of claim 1, wherein the device is configured to release the immobilized nucleic acids by at least one of changing the pH of the biofluid and thereby altering the attractive force of the applied electric field or removing the applied electric field.

8. The device of claim 1, wherein the volume of the chamber is in a range of 10 nL to 100 nL.

9. The device of claim 1, wherein the volume of the chamber is at least 1/50 of the volume of the microfluidic channel.

10. The device of claim 1, further comprising an inlet at a first end of the microfluidic channel to receive the biofluid, and one or more outlets at a second end of the microfluidic channel proximate to the chamber to remove at least some of the biofluid.

11. The device of claim 1, wherein the microfluidic channel in the capture region is configured as a spiral-shaped channel.

12. The device of claim 11, wherein the spiral shaped-channel has a length of at least 40 cm and a diameter of 4 cm or less.

13. A device to capture molecules from a fluid, comprising:
   a substrate formed of a material that is electrically insulating;
   a microfluidic channel made of an electrically insulating material formed on the substrate to carry a biofluid containing molecules including nucleic acids;
   an array of electrodes formed on the surface along a parallel direction of the microfluidic channel constituting a capture region, wherein the array of electrodes are operable to produce an electric field across the microfluidic channel that creates an electrostatic attractive force on the nucleic acids to immobilize them in the capture region; and
   a chamber formed on the substrate of the electrically insulating material and connected to the microfluidic channel, the chamber configured to have a volume less than that of the microfluidic channel and to collect nucleic acids that are released from immobilization in the capture region, wherein the microfluidic channel in the capture region is configured as a spiral-shaped channel.

14. The device of claim 13, wherein the spiral shaped-channel has a length of at least 40 cm and a diameter of 4 cm or less.

15. A device to capture biomolecules from a fluid, comprising:
   a substrate formed of a material that is electrically insulating;
   a microfluidic channel made of an electrically insulating material and formed on the substrate to carry an electrolytic fluid containing biomolecules including nucleic acids and charged particles configured to bind the nucleic acids to a charged surface;

a first chamber region formed in the microfluidic channel, the first chamber region structured to receive the electrolytic fluid containing the nucleic acids attached to the charged particles;

a second chamber region in the microfluidic channel connected to the first chamber region and including one or more outlets to remove at least some of the electrolytic fluid, wherein the second chamber region is configured to have a volume less than that of the first chamber region; and a filter region in the microfluidic channel between the first chamber region and the second chamber region and structured to include holes of a size preventing the particles to pass but allowing the nucleic acids to pass through to the second chamber region, wherein, when the nucleic acids are released from attachment to the charged particles in the filter region, the released nucleic acids are collected in the second chamber region.

16. The device of claim 15, further comprising a mixing region formed in the microfluidic channel as a winding channel to facilitate attachment of the charged particles to the nucleic acids based on electrostatic interactions in the electrolytic fluid, the mixing region including an inlet to receive the electrolytic fluid into the microfluidic channel.

17. The device of claim 15, wherein the biomolecules that are smaller than the size of the holes pass through to the second chamber region to the one or more outlets for removal.

18. The device of claim 15, wherein the filter region is formed of a hydrogel material having nano-scaled pores that block the particles having a micrometer-size.

19. The device of claim 15, wherein the filter region further includes magnetic beads stopped in the filter region by an external magnetic field applied at the filter region, wherein the magnetic beads are introduced into the filter region by flowing the magnetic beads into the device through a second inlet coupled to the first chamber region before receiving the electrolytic fluid.

20. The device of claim 19, wherein the magnetic beads of the filter region are capable of removal when the external magnetic field is removed.

21. The device of claim 19, wherein the size of the holes is adjustable based on a quantity and size of the magnetic beads introduced through the second inlet.

22. The device of claim 15, wherein the particles include silica beads.

23. The device of claim 22, wherein the silica beads are configured as silica-coated magnetic beads.

24. The device of claim 23, wherein the device further includes an applied magnetic field in the first chamber to capture the attached silica-coated magnetic beads and nucleic acids.

25. The device of claim 15, wherein the electrolytic fluid includes a biofluid including at least one of blood, saliva, sputum, urine, vitreous fluid, or fluid derived from a living organism.

26. The device of claim 25, wherein the nucleic acids contained in the blood are at a concentration in a femtomolar (fM) range.

27. The device of claim 15, wherein the nucleic acids include at least one of DNA or miRNA.

28. The device of claim 15, wherein the volume of the second chamber region is in a range of 10 nL to 100 nL.

29. The device of claim 15, wherein the volume of the second chamber region is at least 1/50 of the volume of the microfluidic channel.

30. The device of claim 15, wherein the device is configured to flow the electrolytic fluid through the microfluidic channel at a flow rate of 30 µL/min or less.

31. A device to capture biomolecules from a fluid, comprising:

a substrate formed of a material that is electrically insulating;

a microfluidic channel made of an electrically insulating material and formed on the substrate to carry an electrolytic fluid containing biomolecules including nucleic acids;

a first chamber formed in the microfluidic channel and structured to include two or more regions separated by a porous membrane pre-coated with charged particles configured to bind the nucleic acids to a charged surface, wherein the porous membrane includes a plurality of holes of a size greater than that of the nucleic acids to allow them to pass through the porous membrane and smaller than the charged particles to prevent them to pass through the porous membrane;

a second chamber in the microfluidic channel connected to the first chamber and including one or more outlets to remove at least some of the electrolytic fluid;

a first control valve positioned in the microfluidic between the first chamber and the second chamber to control the flow of the electrolytic fluid between the first and second chambers; and a second control valve positioned in the microfluidic between the second chamber and the one or more outlets to control the flow of the electrolytic fluid out of the device, wherein, when the nucleic acids are released from attachment to the charged particles in a filter region, the released nucleic acids are collected in the second chamber.

32. The device of claim 31, wherein the second chamber is configured to have a volume less than that of the first chamber.

33. The device of claim 31, wherein the volume of the first chamber is in a range of 10 nL to 100 nL.

34. The device of claim 31, wherein the charged particles include silica beads to provide negative surface charge used to attract and bind the nucleic acids.

35. The device of claim 31, wherein the device is configured to introduce an elution buffer to change the pH of the electrolytic fluid in the device and thereby alter the attractive force of the charged particles to release the nucleic acids bound to the charged particles.

36. The device of claim 35, wherein the volume of elution buffer introduced to release the nucleic acids is less than 100 nL.

37. The device of claim 31, wherein the device is configured to flow the electrolytic fluid through the microfluidic channel at a flow rate of 30 µL/min or less.

38. The device of claim 31, wherein the electrolytic fluid includes a biofluid including at least one of blood, saliva, sputum, urine, vitreous fluid, or fluid derived from a living organism.

39. The device of claim 31, wherein the nucleic acids contained in the blood are at a concentration in a femtomolar (fM) range.

40. The device of claim 31, wherein the nucleic acids include at least one of DNA or miRNA.

* * * * *